United States Patent [19]
Smith et al.

[11] Patent Number: 5,169,937
[45] Date of Patent: Dec. 8, 1992

[54] METHOD FOR PRODUCING STABLE GLYCOSYLATED HEMOGLOBIN

[75] Inventors: Richard Smith, Del Mar; Peta-Maree Lamb, San Diego; Linda K. Curtiss, San Diego; Joseph Witztum, San Diego, all of Calif.

[73] Assignee: The Scripps Research Institute, La Jolla, Calif.

[21] Appl. No.: 426,306

[22] Filed: Oct. 24, 1989

Related U.S. Application Data

[62] Division of Ser. No. 932,442, Nov. 18, 1986, Pat. No. 4,876,188.

[51] Int. Cl.$^5$ .......................... C07K 13/00; C07K 9/00
[52] U.S. Cl. ........................................ 530/385; 514/6; 436/67
[58] Field of Search ............................ 530/385; 514/6

[56] References Cited
PUBLICATIONS

Curtiss et al. (Oct. 1983). A novel method for generating region-specific monoclonal antibodies to modified proteins. J. Clin. Inv. 72:1427–1438.

Bisse et al. (Jul. 1982). Quantitation of glycosylated hemoglobin. Elimination of labile glycohemoglobin during sample hemolysis at pH 5. Diabetes 31:630–633.

*Primary Examiner*—Robert A. Wax
*Assistant Examiner*—Richard C. Ekstrom
*Attorney, Agent, or Firm*—Douglas A. Bingham

[57] ABSTRACT

Methods of preparing glucitollysine-hemoglobin from a sample of glucohemoglobin containing stable and labile glucohemoglobins and for assaying for the presence of stable glucohemoglobin are disclosed, as is a diagnostic assay system useful for carrying out the methods.

5 Claims, 13 Drawing Sheets

METHOD FOR PRODUCING STABLE GLYCOSYLATED HEMOGLOBIN

This invention was made with the support of the Government of the United State of America, and the Government of the United States of America has certain rights in the invention.

This is a division of application Ser. No. 06/932,442 filed Nov. 18, 1986, now U.S. Pat. No. 4,876,188.

DESCRIPTION

1. Technical Field

This invention relates to a method of assaying the amount of stable glycohemoglobin in a body sample. More specifically, this invention relates to a method of optimizing and analyzing the number of glycitollysine-containing epitopes on a reduced glycohemoglobin molecule.

2. Background of the Invention

Glycosylated hemoglobins (glycohemoglobins) are hemoglobins that are covalently bound to a sugar moiety. That is, glycohemoglobins are the addition products (adducts) of the reaction between hemoglobin and a sugar. Glucohemoglobins are a subclass of glycohemoglobin that comprise hemoglobin bound to glucose. Glycosylation is a nonspecific reaction that has been reported to result in the addition of various sugars or sugar phosphates to human hemoglobins $A_0$, $A_2$, C, D, E, F and S.

Glucohemoglobin $A_{1c}$ ($HbA_{1c}$) is the most abundant and most extensively studied glycohemoglobin. $HbA_{1c}$ represents $HbA_0$ having D-glucose bound to the amino group of the N-terminal valine of one or both of the beta-globin chains. However, the addition of glucose to hemoglobin is not limited to the N-terminus of the beta-chain and can also occur at the epsilon amino group of lysines in both the alpha- and beta-globin chains.

The reaction mechanism and kinetics of glucose addition to hemoglobin is shown schematically in FIG. 1. D-Glucose in its aldehyde form reacts rapidly and reversibly with an amino group (provided by an N-terminal valine or by the epsilon amino group of an intrachain lysine residue) to form a labile aldimine (Schiff base) intermediate. This labile intermediate (labile glucohemoglobin) can dissociate back to D-glucose and hemoglobin, or it can undergo an irreversible but slow Amadori rearrangement to form a stable ketoamine (stable glucohemoglobin). The ketoamine in turn exists in equilibrium with a hemiketal or ring form (specifically, deoxyfructosyl-lysine).

The formation of stable glucohemoglobin is a nonenzymatic process that proceeds slowly and continuously throughout the lifespan of the erythrocyte. The rate of glucohemoglobin formation is directly dependent on an individual's ability to control blood sugar (glucose) levels. Therefore, information as to the concentration of total stable glucohemoglobin of $HbA_{1c}$, has gained acceptance as providing an objective, time-averaged monitor for glycemic control in diabetes mellitus patients.

The various methods for assaying the amount of total glycohemoglobin or a particular glucohemoglobin species such as $HbA_{1c}$, and the methodological problems associated with those procedures have been reviewed in Goldstein et al., *Clin. Chem.*, 31:1060–1067 (1985) and Jovanovic et al., *Am. J. Med.*, 70:331–338 (1981). For instance, the radioimmunoassay (RIA) for $HbA_{1c}$ described by Javid et al., *Br. J. Haematology*, 38:329–337 (1978), suffers from the use of antibodies having low affinity and cross-reactivity with nonglucosylated hemoglobin.

More recently, Curtiss et al., *J. Clin. Invest.*, 72:1427–38 (1983) reported the use of monoclonal antibodies that immunoreact with glucitollysine residue-containing epitopes to assay for the presence of glucosylated plasma proteins having relatively short half-lives. Those workers also reported the inhibition of binding of some of their monoclonal antibodies to glucitollysine-plasma proteins by glucitollysine-hemoglobin.

A glucitollysine residue is produced by reduction of the before-discussed Amadori rearrangement product when the ketoamine form of the glucosylated epsilon amino group of lysine (Amadori product) is reduced by a water-compatible borohydride reducing agent (reductant) such as sodium borohydride or sodium cyanoborohydride. Thus, Curtiss et al. showed that the glucoplasma protein in a sample can be reduced and converted into glucitollysine-containing plasma protein, and subsequently assayed using glucitollysine-specific monoclonal antibodies, thereby overcoming the problem of cross-reactivity observed with nonglucosylated plasma proteins.

However, as can be seen from FIG. 1, the in vitro reduction process produces glucitollysine residues in both the labile and stable forms of glucohemoglobin. Thus, without more, the method of Curtiss et al., supra, as applied to hemoglobin instead of a plasma protein could not distinguish between the amount of labile and stable forms of glucohemoglobin present in a sample.

According to both the Goldstein et al., supra, and Jovanovic et al., supra, reviews, in order for a glucohemoglobin assay to provide a reliable index of long-term glucemic control, the assay method must distinguish between the labile and stable forms of glucohemoglobin. There are two reasons for this.

First, at any given point in time, the total amount of glucohemoglobin present in an erythrocyte is the sum of both the labile and stable fractions. Second, the amount labile glucohemoglobin present in erythrocytes rapidly fluctuates in response to short-term glucose levels. That is, the formation of the labile fraction is sufficiently fast compared to the slow, irreversible formation of the stable ketoamine that acute changes in blood glucose will result in an increase in the total glucohemoglobin substantially as a result of an increase of the labile fraction. Therefore, inclusion of the labile fraction in any measurement of glucohemoglobin may reflect an acute or short-term response to blood glucose levels and may not reflect the degree of long-term glucemic control.

The currently available chromatographic, electrophoretic and immunologic methods for assaying glycohemoglobin can not distinguish between the labile and stable forms of glucohemoglobin when both are present in the sample. Accordingly, there has been a substantial amount of research into developing assay methods that include a procedure for removing the labile glucohemoglobin fraction from the sample prior to the assaying step.

Reported methods for eliminating labile glucohemoglobin from a sample typically rely on subjecting the sample to conditions that favor dissociation of the labile form into a glycose such as glucose (an aldose) and hemoglobin. Those methods include incubation of the erythrocytes in normal saline for 24 hours prior to hemolysis [Goldstein et al., *Diabetes* 29:623–28 (1980)], dialysis of the hemolysate for 48 hours against glucose-free phosphate buffer, [Widness et al., *J. Lab. Clin. Med.* 95:386–394 (1980)], and dilution and subsequent concentration by ultrafiltration of the hemolysate [Innanen et al., *Clin. Chem.* 27:1478–79 (1981)].

Of particular interest with regard to the present invention are those methods that use an acidic incubation step for the removal of labile glycohemoglobin. Nathan et al., *Diabetes*, 30:700–701 (1981) describes an assay method wherein erythrocytes are incubated in a solution containing semicarbazide and analine at pH 5 for 30 minutes at 38 degrees C. to deplete (remove) the labile fraction. The stable glycohemoglobin, e.g., glucohemoglobin, fraction is then assayed using either high-pressure liquid chromatography (HPCL) or citrate agar gel electrophoresis separation techniques.

The method described by Bisse et al., *Diabetes*, 31:630–633 (1982) removed the labile fraction from the sample to be assayed by lysing the erythrocytes in 50 volumes of a solution containing 0.05 M potassium biphthalate at pH 5 for 15 minutes at 37 degrees C. The amount of stable glycohemoglobin remaining in the labile glycohemoglobin-depleted sample was then determined by HPLC.

However, there have been no reports to date concerning the use of an acidic, labile glycose-, e.g., glucose-, depletion step, using biphthalic acid or otherwise, in combination with a reduction step using a water-compatible borohydride reductant to form glucitollysine-hemoglobin that is immunologically assayable.

SUMMARY OF THE INVENTION

The present invention contemplates a method of assaying the amount of stable glycohemoglobin such as glucohemoglobin in a glycohemoglobin sample. The labile glucohemoglobin present in the sample is first removed by admixing the glucohemoglobin-containing sample with phthalic or biphathalic acid at a ratio of at least about 1.5 micromoles of acid per milligram of hemoglobin in an aqueous medium at a pH value of about 3 to about 6 to form an acid reaction admixture. That admixture is maintained for a predetermined period of time and under predetermined conditions as to permit the labile glucohemoglobin present to dissociate into glucose and hemoglobin, while maintaining the stable glucohemoglobin present in the original sample.

The acid reaction admixture is then admixed with a water-compatible borohydride, preferably sodium or potassium borohydride, at a ratio of at least about 0.15 micromoles of borohydride per milligram of hemoglobin to form an aqueous reduction reaction admixture. The reduction reaction admixture is maintained for a predetermined time period and under such conditions as to convert the glucosylated-lysines present to glucitol-lysine residues and form glucitollysine-hemoglobin.

After separating any unreacted borohydride from the glucitollysine-hemoglobin present in the reduced sample the amount of glucitollysine-hemoglobin present is determined by well known immunologic assay methods that utilize glucitollysine-specific receptor molecules. It is to be understood that this method, up to the immunological determination of glucitollysine-hemoglobin, can also be utilized to prepare glucitollysine-hemoglobin from stable glucohemoglobin in a glucohemoglobin sample that contains both labile glucohemoglobin and stable hemoglobin.

The invention also contemplates a diagnostic system that is typically in kit form and contains a plurality of separate packages. A first package contains a solid phase matrix such as a microtiter plate on whose well surfaces the assay can be carried out. A second package contains a predetermined amount of the water-compatible borohydride reductant in solid form. A third package contains appropriate glucitollysine-specific receptor molecules in dry or liquid form. A fourth package contains phthalic or biphtalic acids. The system can further include one or more additional packages that contain one or more additionally useful reagents.

The present invention provides several benefits and advantages.

One benefit is that the concentration of stable hemoglobin in a glucohemoglobin sample containing both labile and stable glucohemoglobins can be assayed relatively quickly, easily and accurately.

One advantage of the present invention is that glucitollysine-hemoglobin can be prepared from the stable glucohemoglobin portion of a glucohemoglobin sample to the exclusion of glucitollysine-hemoglobin prepared from the labile glucohemoglobin portion of the sample.

Yet another benefit of the invention is that the glucitollysine-hemoglobin prepared is more antigenic than is that prepared by other means.

Still further benefits and advantages of the present invention will be apparent to those skilled in the art from the description that follows.

BRIEF DESCRIPTION OF THE DRAWINGS

In the Figures forming a portion of this disclosure.

Panel 2A illustrates the results obtained using glucitollysine (▲); reduced poly-L-lysine (□); reduced alpha-T-Boc-lysine (●); reduced nonglucosylated hemoglobin (Δ); and reduced poly-L-valine as potential competitors (■). Those results indicate that of this group, only the positive control, glucitollysine, inhibited the binding of HRPO-G6C9 receptors, and therefore reduction alone, in the absence of glucose, does not produce the epitope recognized by HRPO-G6C9.

Panel 2B illustrates the results obtained using glucitollysine (▲); glucosylated poly-L-lysine (□); glucosylated alpha-T-Boc-lysine (●); glucosylated hemoglobin (Δ) and glucosylated poly-L-valine (■) as potential competitors. Those results indicate that only the positive control glucitollysine inhibited binding. Thus, glucosylation alone does not produce the epitope recognized by HRPO-G6C9.

Panel 2C illustrates the results obtained after glucosylating and then reducing poly-L-lysine (□); alpha-T-Boc-Lysine (●); hemoglobin (Δ) and poly-L-valine (■). Those results indicate that when poly-L-lysine and hemoglobin are glucosylated and reduced they both can compete for HRPO-G6C9 antibody combining sites in a manner similar to that of the positive control glucitollysine. Only glucosylated and reduced poly-L-valine failed to significantly compete, thus indicating that HRPO-G6C9 receptors do not immunoreact with the N-terminal glucosylated valine of hemoglobin.

FIG. 3 contains two graph panels that illustrate the unexpected results obtained when glucitollysine formation in a hemoglobin sample is carried out by reduction in the presence of phthalic acid.

In panel 3A, glucohemoglobin-containing hemoglobin samples were provided as 10 microliters (ul) of a packed RBC pellet obtained from the blood of either a diabetic individual (triangle), or a normal individual (squares). The samples were reduced using either $NaBH_4$ (Δ,□) or $KBH_4$ (▲,■) as water-compatible borohydride reductant and then assayed for glucitollysine-hemoglobin formation. The hemoglobin concentration in each of the reduction reaction admixtures was 2.4 milligrams per milliliter (mg/ml). The concentration of the borohydride in each of the admixtures is shown on the abscissa.

Panel 3B illustrates the results obtained for the same two hemoglobin samples and same two reductants when reduction was carried out after reaction of the samples with phthalic acid. A comparison of the results in panel 3A with those in panel 3B indicates that reaction with phthalic acid prior to reduction with borohydride results in a significant increase in assayable glucitollysine-hemoglobin, as determined by immunologic binding of the HRPO-G6C9 receptors. The glucitollysine-hemoglobin prepared as described using phthalic acid and a borohydride reductant thus exhibits increased antigenicity. This observed increased amount of assayable glucitollysine-hemoglobin (antigenicity) was unexpected.

Figure 4:
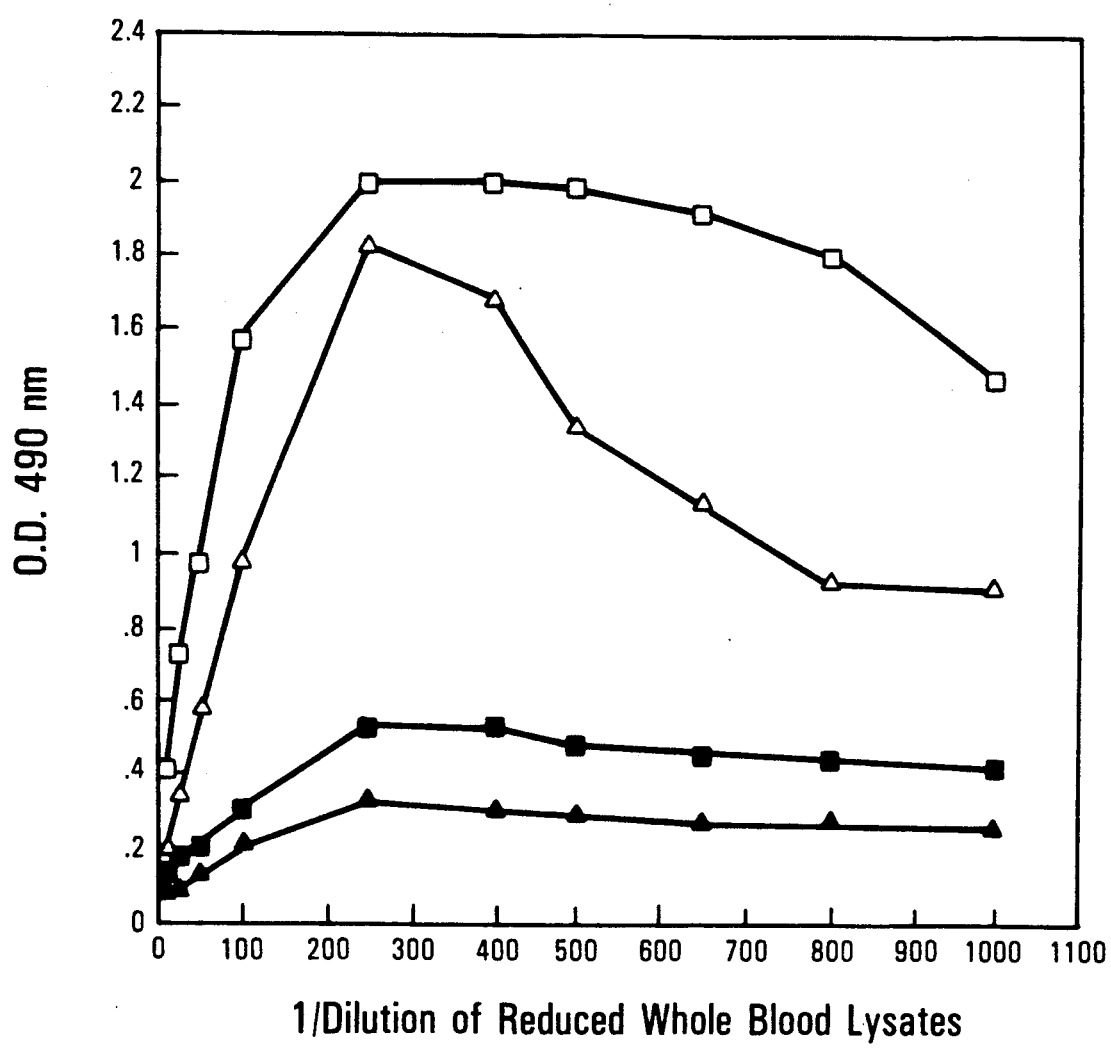

FIG. 4 illustrates the effect of varying the maintenance time period of the reduction reaction admixture. Acid reaction admixtures prepared using various dilutions of whole blood from either a diabetic or normal female were admixed with an equal volume of 0.10 M phthalic acid. The concentration of hemoglobin (Hb) in the acid reaction admixtures was, in mg Hb/ml, as follows: 27.0, 10.8, 5.4, 2.7, 1.08, 0.675, 0.54, 0.415, 0.337, and 0.270. The micromoles of acid per milligram of hemoglobin ratio in each of the above admixtures was 1.85, 4.63, 9.26, 18.5, 46.3, 74.07, 92.6, 120.5, 148.5 and 185.2, respectively.

After hemolysate formation, reduction reaction admixtures were prepared by admixing each hemolysate with an equal volume of 400 mM $NaBH_4$. The reciprocals of the final dilutions of the hemoglobin samples are shown on the abscissa. From left to right and in the order of increasing hemoglobin dilution, the ratio of millimoles $NaBH_4$ per milligram hemoglobin of each of the reduction admixtures shown was 0.0148, 0.037, 0.074, 0.148, 0.37, 0.593, 0.74, 0.964, 1.187, and 1.481.

The results shown in FIG. 4 indicate that maintenance of the reduction reaction admixtures for 30 minutes for both the diabetic (□) and normal (■) samples produced more assayable glucitollysine-hemoglobin than did a 15 minute maintenance of those admixtures for both the diabetic (Δ) and normal samples (▲).

Figure 5:
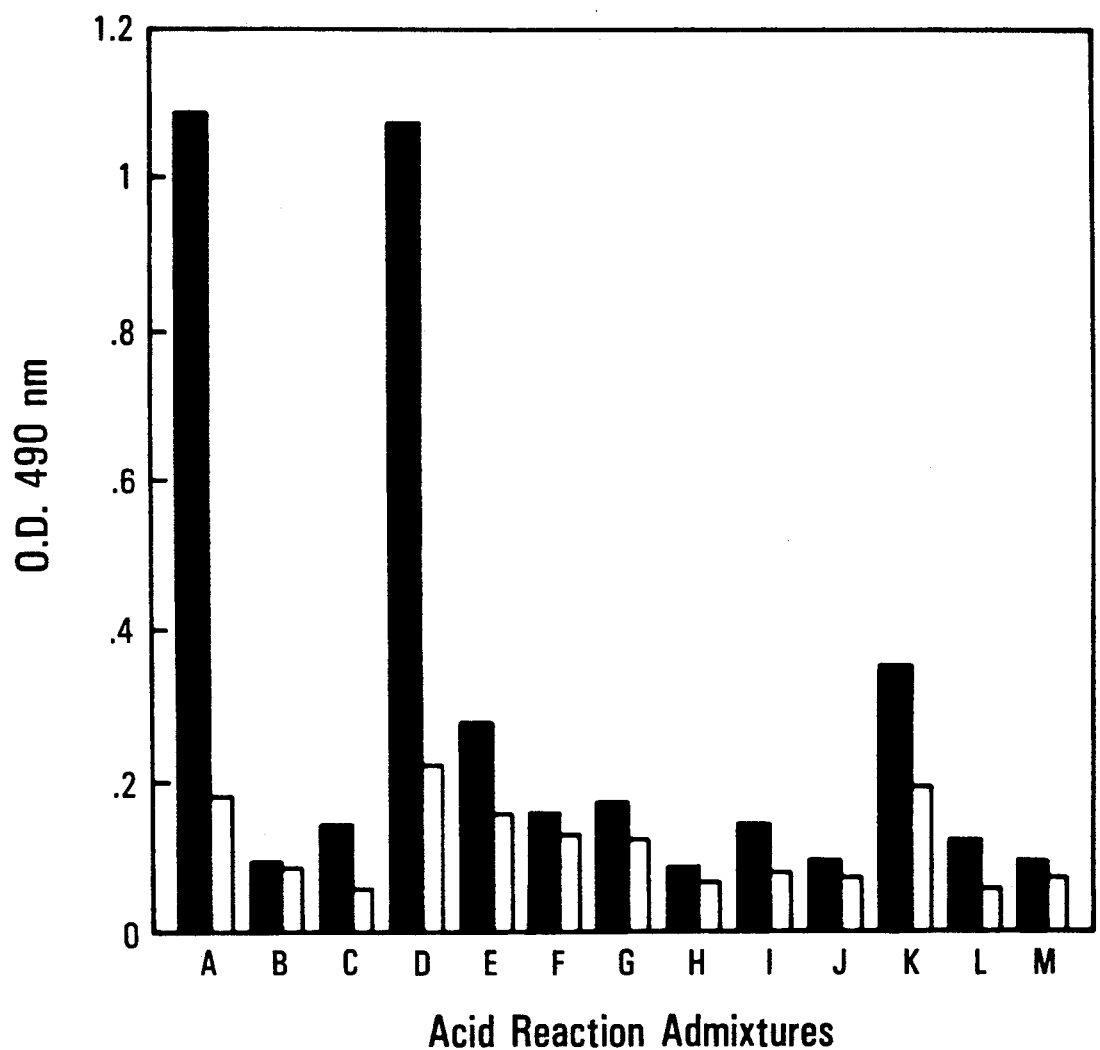

FIG. 5 is a bar graph illustrating the effect of various acid reaction admixtures on the formation of assayable glucitollysine-hemoglobin as a function of the acid of the reaction admixtures. The admixtures were prepared by admixing 10 microliters of a packed RBC pellet obtained from either a diabetic (■) or normal (□) blood sample and 615 microliters of one of the following 0.05 M, pH value 4 to 5, solutions: phthalic acid (A), citrate (E), acetic acid (F), phosphate (G), D(+) glucosamine (H), alpha-ketoglutaric acid (I), oxalacetic acid (J), oxalic di-potassium acid (K), succinic acid (L), and pyruvic acid (M), followed by reduction with $NaBH_4$ and determination of the glucitollysine-hemoglobin content by the ELISA described hereinafter. Controls included distilled water (B), overnight (about 18 hours) incubation of the RBCs in isotonic saline followed by distilled water (C) or phthalic acid (D). Controls were assayed as described above. The amount of assayable glucitollysine-hemoglobin formation is expressed as an optical density value (O.D.) at 490 nm.

The results shown in FIG. 5 indicate that the classic method for removing the labile glucohemglobin from a sample; i.e, overnight incubation of the RBCs in saline (C), does not potentiate the formation of glucitollysine in the same manner as phthalic acid. Those results also illustrate the potentiation of assayable glucitollysine using a combination of phthalic acid and a water-compatible borohydride reductant.

Figure 6:
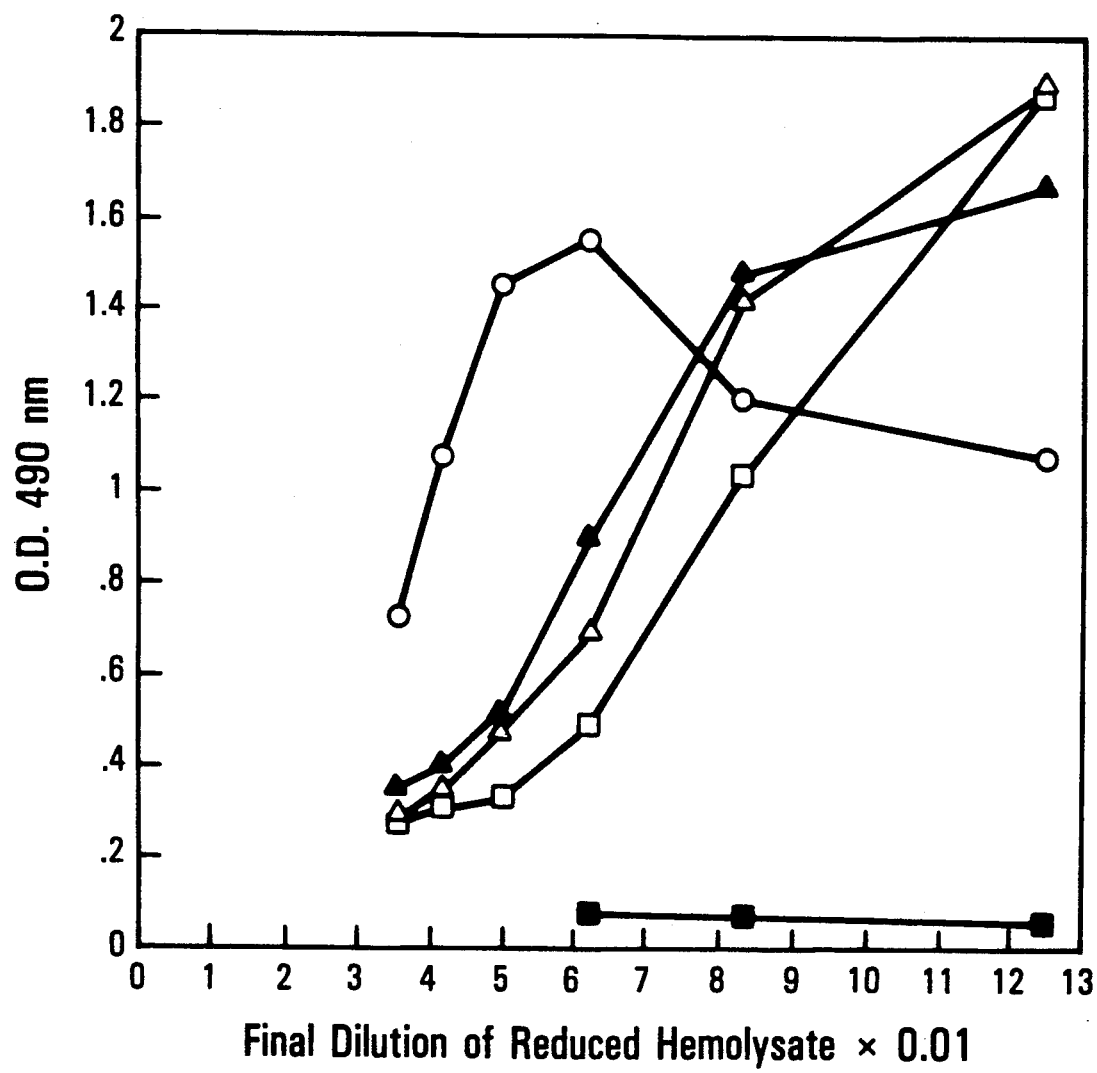

FIG. 6 is a graph illustrating the results obtained when the assay method of the present invention was performed with acid reaction admixtures having concentrations of either about 0.05 M (○) or about 0.025 M (▲) phthalic acid. Also shown are the acid reaction admixture having a concentration of 0.05 M phthalic acid were not subjected to reduction (■). Other controls include the results obtained when no phthalic acid treatment was used prior to $NaBH_4$ reduction (Δ) and incubation of the RBCs overnight in isotonic saline prior to reduction, but without phthalic acid treatment (▲).

The concentrations of hemoglobin in the acid reaction admixtures were in mg/ml, 75, 50, 37.5, 30; 25 and 21.4. The concentrations of hemoglobin in each of the respective reduction reaction admixtures were, in mg/ml 37.5, 25, 18.75, 15, 12.5 and 10.7. The concentration of $NaBH_4$ in the reduction reaction admixtures was 200 mM.

Figure 7:
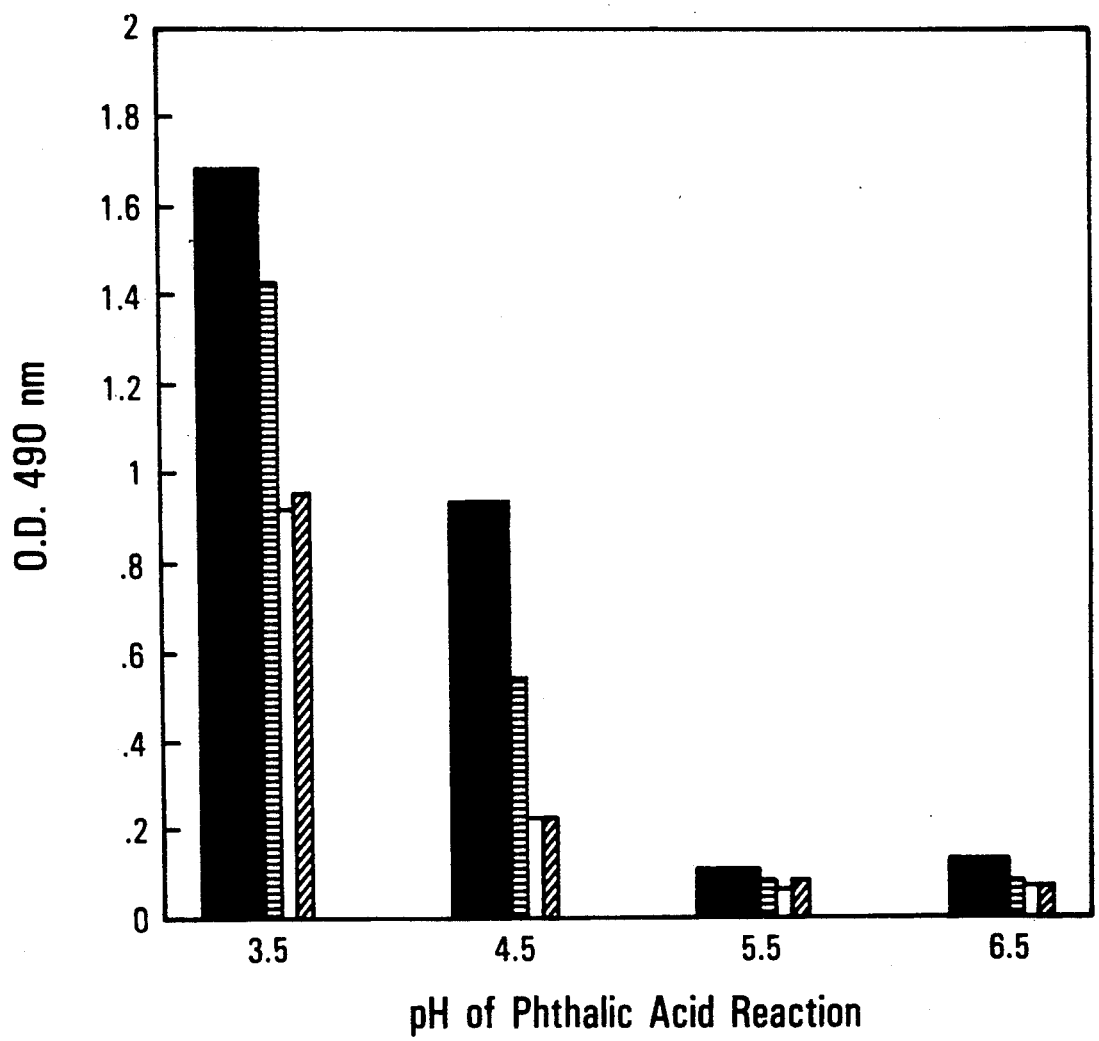

FIG. 7 is a bar graph illustrating the O.D. 490 values obtained using aqueous phthalic acid solutions having pH values of 3.5, 4.5, 5.5 and 6.5 to prepare acid reaction solutions. Diabetic hemoglobin samples number 1 (■) and number 2 (▨) and normal samples number 1 (□) and number 2 (▨) had total glycosylated hemoglobin levels of 14.7 percent, 10.7 percent, 7.5 percent and 8.0 percent, respectively, as determined using the Gly-Affin System (Isolab, Akron, OH) according to the manufacturer's instructions.

Figure 8:
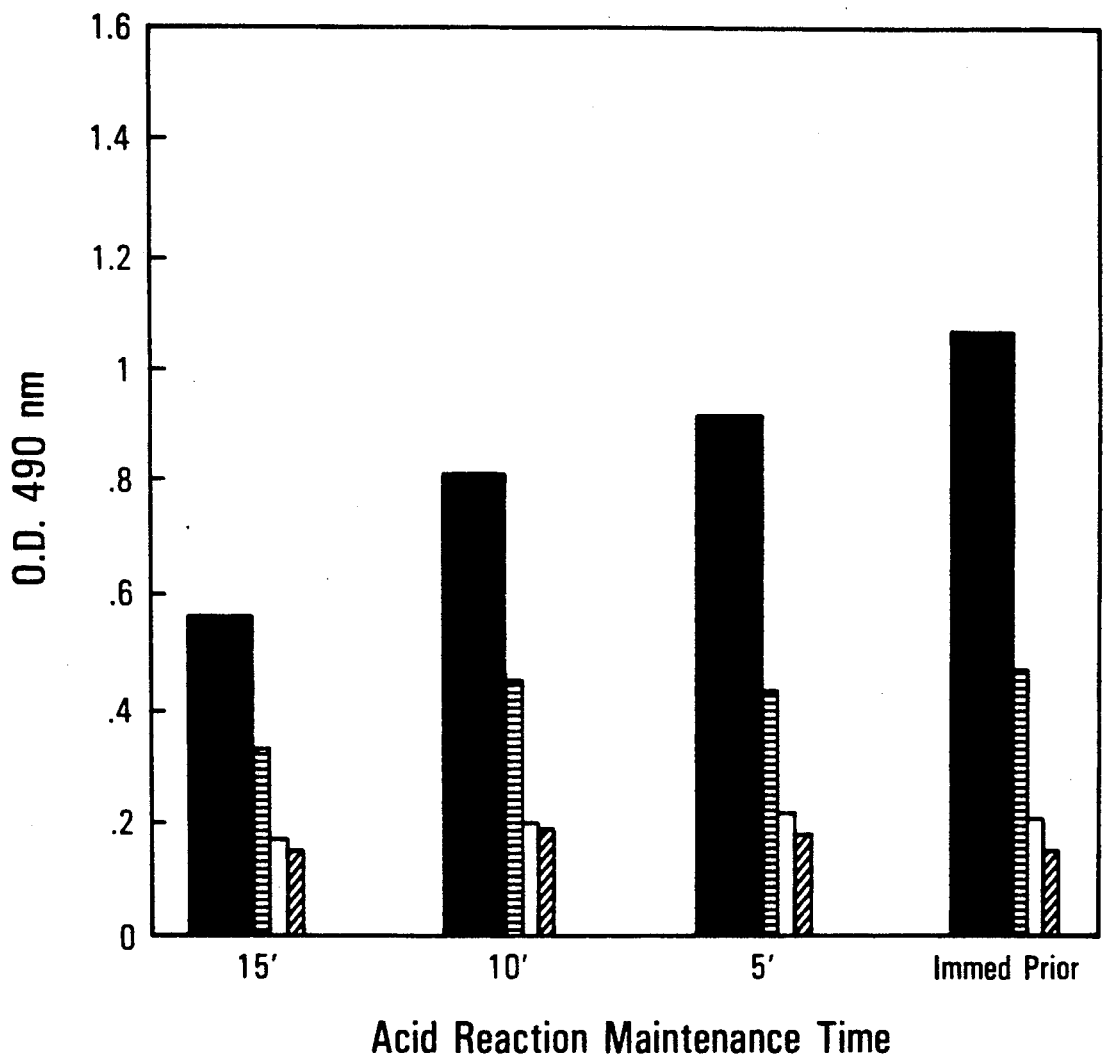

FIG. 8 is a bar graph illustrating the effect of varying the acid reaction admixture maintenance time periods. The admixtures were formed using 0.05 M phthalic acid having an unadjusted pH value of about 4.3. The samples used were the same as those described in FIG. 7; i.e., diabetic number 1 (■), diabetic number 2 (▨), normal number 1 (□) and normal number 2 (▨).

Figure 9:
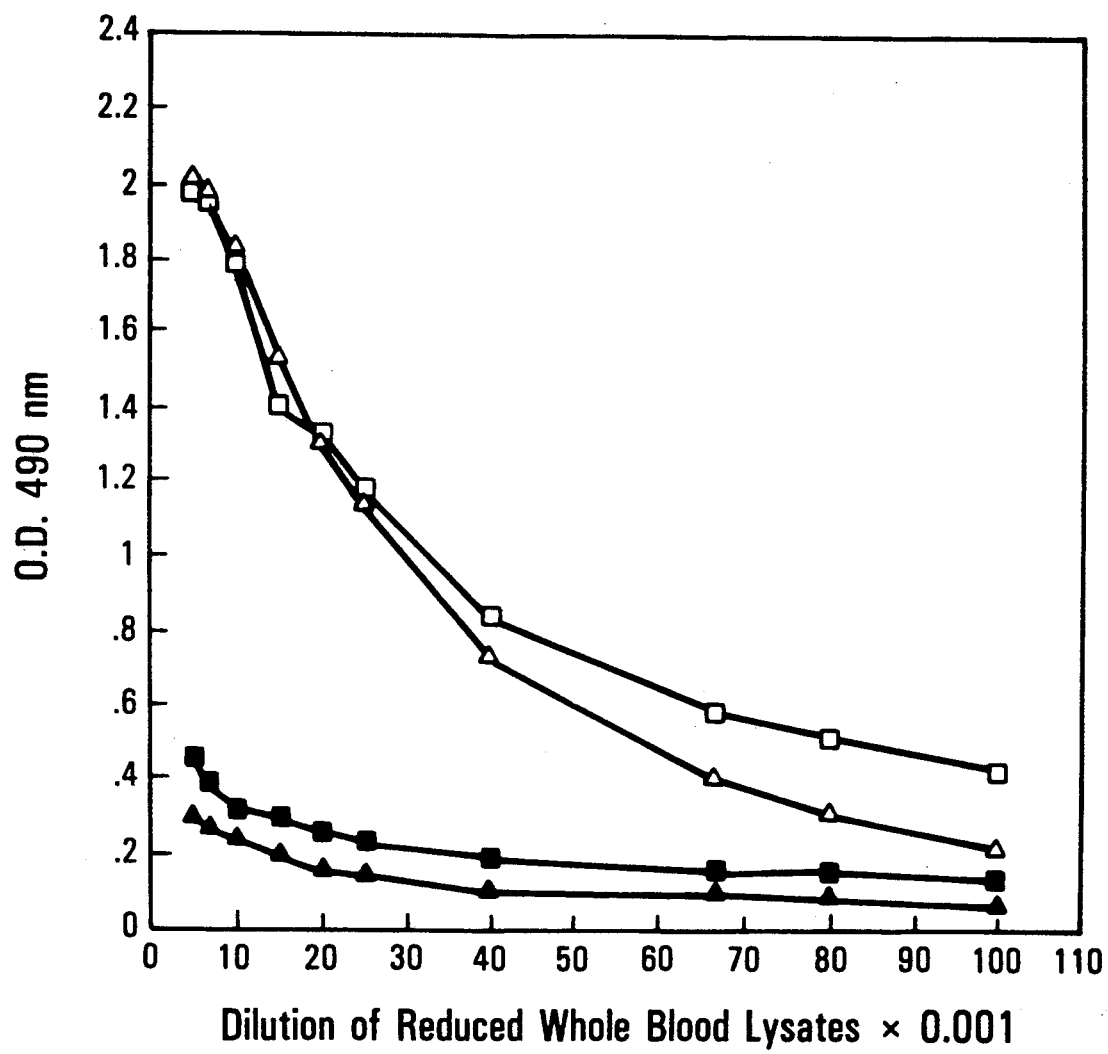

FIG. 9 illustrates the effect of maintaining the reduction reaction admixtures at either room temperature or at 37 degrees C. using hemoglobin at concentrations ranging from 27.0 mg/ml to 0.27 mg/ml in the acid reaction admixtures and 13.5 mg/ml to 0.135 mg/ml in the reduction reaction admixtures. The acid reactions were performed at a phthalic acid concentration of about 0.05 M and at a nonadjusted phthalic acid pH value (about 4.3). Reduction reactions were performed at a NaBH$_4$ concentration of about 200 mM.

Hemoglobin samples provided as whole blood from either a diabetic (open symbol) or normal (closed symbol) female were maintained in the reduction reaction at either room temperature (Δ and ▲, respectively) or 37 degrees C. (■ and □, respectively).

Figure 10:
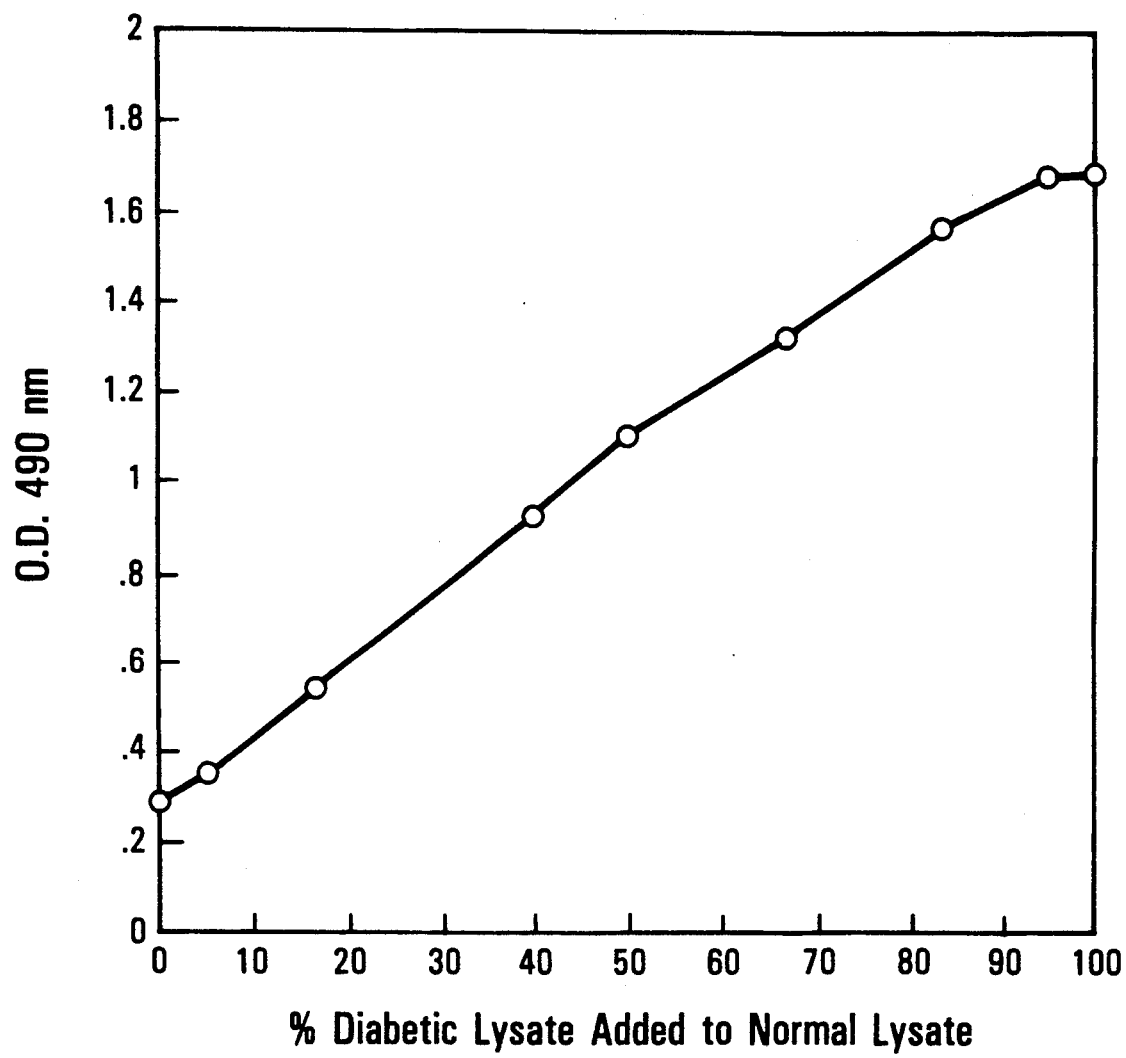

FIG. 10 shows the results of the spike and recovery study wherein hemoglobin samples containing the various shown ratios of a normal and a diabetic blood sample were assayed. The percent total glycosylated hemoglobin in the non-mixed diabetic and normal sample was determined using the Gly-Affin System (Isolab) and found to be 18.56 percent and 5.45 percent, respectively. Further details of this study are provided in Example 8.

DETAILED DESCRIPTION OF THE INVENTION

A. Definitions

The term "antibody" refers to a molecule that is a member of a family of glycosylated proteins called immunoglobulins that can specifically combine with an antigen. Such an antibody combines with its antigen by a specific immunologic binding interaction between the antigenic determinant of the antigen and the antibody combining site of the antibody.

An "antibody combining site" is that structural portion of an antibody molecule comprised of heavy and light chain variable and hypervariable regions that specifically binds antigen. Using the nomenclature of Jerne, (1974) *Ann. Immunol. (Inst. Pasteur)*, 125C:373–389, an antibody combining site is also referred to as a "paratope".

Antibody combining site-containing (paratope-containing) polypeptide portions of antibodies are those portions of antibody molecules that contain the paratope and bind to an antigen, and include, for example, the Fab, Fab', F(ab')$_2$ and F(v) portions of the antibodies. Fab and F(ab')$_2$ portions of antibodies are prepared by the proteolytic reaction of papain and pepsin, respectively., on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. Intact antibodies are preferred, and are utilized as illustrative of the monoclonal ligand molecules of this invention.

The word "antigen" has been used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, it will generally be termed an antigen.

The phrase "antigenic determinant" refers to the actual structural portion of the antigen that is immunologically bound by an antibody combining site. The Jerne nomenclature redefines an antigenic determinant as an "epitope".

The term "biologically active" refers at least to the ability of a proteinaceous molecule to specifically bind antigen or specific antibody combining site, although other general or effector capability may also be present in that molecule. Biological activity of a receptor molecule containing an antibody combining site is evidenced by the immunologic reaction of the paratope (antibody combining site) with its epitope (antigenic determinant) upon their admixture in an aqueous medium to form an immunoreactant, at least at physiological pH values and ionic strengths. Preferably, biological activity occurs under biological assay conditions that are defined hereinafter.

"ELISA" refers to an enzyme-linked immunosorbent assay that employs an antibody or antigen bound to a solid phase and an enzyme-antigen or enzyme-antibody conjugate to detect and quantify the amount of antigen or antibody present in a sample. A description of the ELISA technique is found in Chapter 22 of the 4th Edition of *Basic and Clinical Immunology* by D. P. Sites et al., published by Lange Medical Publications of Los Altos, CA in 1982 and in U.S. Pat. Nos. 3,654,090; 3,850,752; and 4,016,043, which are all incorporated herein by reference.

"Enzyme" refers to a protein capable of accelerating or producing by catalytic action some change in a substrate for which it is often specific.

The term "immunoreact" in its various forms means binding between a receptor molecule and an epitope.

"Immunoreactant" as used herein refers to the product of an immunological reaction; i.e., that entity produced when a receptor molecule immunologically binds to an epitope.

The terms "labeling means", "indicating group" or "label" are used interchangeably herein to include single atoms and molecules that are either directly or indirectly involved in the production of a detectable signal to indicate the presence of a immunoreactant. Any labeling means can be linked to or incorporated in a receptor or used separately, and those atoms or molecules can be used alone or in conjunction with additional reagents. Such indicating groups or labels are themselves well-known in immunochemistry and constitute a part of this invention only insofar as they are utilized with otherwise novel, methods and/or systems.

The term "receptor" is used herein to indicate a biologically active molecule comprised of an antibody combining site that immunologically binds to (or with) an antigen. Such binding typically occurs with an affinity of about $10^5$ to about $10^{10}$ liters per mole and is a specific interaction of the epitope of the antigen with the antibody combining site of the receptor.

The words "secrete" and "produce" are often used interchangeably in the art to refer to cells from which antibody molecules are obtained. Cells that produce antibodies may, however, not secrete those molecules into their environment. The hybridoma cells of interest herein secrete monoclonal antibodies into their environment. Nevertheless, such cells are sometimes referred to herein as "antibody-producing" cells, and their antibodies are sometimes referred to as being "produced" in keeping with the phrase utilized in the art. Antibody combining site-containing portions of the above antibodies (receptors) are similarly referred to herein as being "produced" or "secreted", although it is to be understood that such molecules are prepared from antibodies that are themselves "produced" or "secreted".

The term "supernatant" is used herein to refer to the in vitro liquid medium in which cells are cultured. Monoclonal antibodies produced by the hybridoma cultures of interest herein are secreted into their culture medium environment. Therefore the culture medium supernatant for those cells is one preferred source of the monoclonal receptor molecules and is readily obtainable free from hybridoma cells by well known techniques. Exemplary of such techniques is low speed centrifugation to sediment cells out of the liquid medium. Monoclonal receptor molecules can alternatively be obtained from ascites tumor fluid (ascites fluid) of laboratory animals into which the hybridoma tissue was introduced. Both methods are well known in the art. Monospecific receptor molecules also discussed herein are secreted into the blood of the host animals in which they are raised. Methods of obtaining such antibodies are also well known in the art.

B. Glucitollysine-Hemoglobin

Production Methods

The present invention contemplates a method of producing glycitollysine-hemoglobin from glycohemoglobin, using glucitollysine-hemoglobin and glucohemoglobin as exemplary. The glucitollysine-hemoglobin produced by this method has an unexpected increased antigenicity relative to glucitollysine-hemoglobin produced by methods known in the art. The reason for the observed increased antigenicity is unknown.

A sample of glucohemoglobin having a known amount of hemoglobin is provided. The glucohemoglobin so provided can be present as contained in erythrocytes (red blood cells) or as free molecules.

Methods for obtaining glucohemoglobin as well as determining the presence of glucohemoglobin are well known in the art. In addition, methods for glucosylating proteins and polypeptides in general and hemoglobin in particular are well known in the art. See, for example., U.S. Pat. No. 4,478,744 to Mezci et al., and Curtiss et al., *J. Clin. Invest.*, 72:1427-38 (1983), whose disclosures are incorporated herein by reference.

Typically, a glucohemoglobin sample is provided as a known amount of whole blood and more preferably as a known volume of packed red blood cells (RBC). Methods for providing samples of blood and packed red blood cells as well as methods for lysing the RBCs contained therein are well known in the art.

(a) The glucohemoglobin hemoglobin sample is admixed in an aqueous medium with a known amount of phthalic acid or biphthalic acid to form an acid reaction admixture. The amount of acid admixed is that amount sufficient to provide a ratio of at least about 1.5 micromoles of phthalic acid per milligram of hemoglobin, preferably a ratio of at least about 15.0 micromoles of acid per milligram of hemoglobin and more preferably at least about 45.0 micromoles acid per milligram of hemoglobin.

The acid is typically provided as an aqueous solution having a pH value of about 3 to about 6, preferably about 4 to about 5, and more preferably about 4.1 to about 4.5. The aqueous medium provided by the acid solution can thus provide the aqueous medium of the acid reaction admixture.

Methods for determining the molar amount of hemoglobin in a sample are well known in the art.

(b) The obtained acid reaction admixture is maintained for a predetermined period of time from seconds to hours. A time period of about 10 minutes to about 15 minutes usually is sufficient to substantially dissociate and remove (deplete) any labile glucohemoglobin present, while maintaining the stable glucohemoglobin originally present in the sample. However, if desired, the admixture may be maintained for a time period of about 16 to about 20 hours without any deleterious consequences.

When the sample of glucohemoglobin is provided as whole RBCs, the acid solution acts as a red blood cell lysing solution (agent) so that during the acid reaction maintenance period the RBCs are lysed thereby releasing the hemoglobin contained therein to form a hemolysate. The hemolysate so formed is depleted of labile glucohemoglobin and contains the stable hemoglobin present in the original RBC sample portion.

(c) The acid reaction admixture is subsequently admixed with a water-compatible borohydride reductant to form an aqueous reduction reaction admixture. The aqueous portion of the reduction reaction admixture can be supplied by the water of the acid reaction mixture, by an aqueous solution of the borohydride reductant, or separately. Preferably, the acid reaction admixture provides at least a portion of the aqueous portion of the reduction reaction admixture.

Water-compatible borohydride reductants are well known in the art and include sodium borohydride ($NaBH_4$), potassium borohydride ($KBH_4$) and sodium cyanoborohydride ($NaCNBH_3$). The amount of borohydride that is admixed is that amount sufficient to provide a ratio of at least about 0.015 millimoles of borohydride ($BH_4^-$) per milligram of hemoglobin, preferably an amount sufficient to provide a ratio of at least about 0.15 millimoles of borohydride per milligram of hemoglobin and more preferably an amount sufficient to provide a ratio of at least about 0.35 millimoles of borohydride per milligram of hemoglobin.

(d) The obtained reduction reaction admixture is maintained, at a temperature above about 0 degrees C. to about 37 degrees C., preferably about 20 degrees C. to about 37 degrees C., for a predetermined period of time from seconds to hours. A time period of about 10 minutes to about 16-20 hours, preferably about 15 minutes to about 30 minutes, is usually sufficient to reduce the keto group(s) contained in the stable glucohemoglobin into hydroxyl group(s) of glucitollysine residue(s) and form glucitollysine-hemoglobin (e) The obtained glucitollysine-hemoglobin is then separated from the remaining unreacted borohydride to form isolated glucitollysine-hemoglobin. The cellular debris from RBC lysis is also preferably removed in this separation step.

Methods of separating the glucitollysine-hemoglobin from the nonreacted borohydride, and the remainder of the reduction reaction admixture, are also well known in the art. Such separation methods include gel exclusion chromatography, electrophoresis, affinity chromatography and the like. Where a solid phase assay method is utilized, it is preferred to bind the hemoglobin derivative to the solid phase matrix utilized to form a solid support, and thereafter simply decant the liquid reduction reaction mixture from the solid phase to perform the separation. The solid support containing the bound glucitollysine can also be washed after the decanting step.

The above-described method can be used to produce glucitollysine-hemoglobin useful in diagnostic assay methods and kits that are used to measure glucohemoglobin. That method can be used to produce other desired glycitollysine-hemoglobin species, depending on the particular lysine-sugar adduct present.

C. Assay Methods

The present invention also contemplates a method of determining the amount of stable glycohemoglobin in a hemoglobin sample, again using glucohemoglobin as exemplary.

The before-described method of producing glucitollysine-hemoglobin is used to prepare isolated glucitollysine-hemoglobin of step (e), above, from a sample containing a known amount of hemoglobin. Subsequently, the following steps are performed.

(f) The isolated glucitollysine-hemoglobin is admixed with receptors that immunoreact with glucitollysine-containing epitopes and are substantially free of cross-reactivity with glucitollysine-free hemoglobin to form an immunoreaction admixture. The useful receptors are typically admixed in stoichiometric excess over the amount of glucitollyine expected to be present.

Receptor molecules exhibiting the above-described immunoreactivities are referred to herein as "glucitollysine-specific" receptor molecules or receptors. It is to be understood that such receptor molecules can cross-react with other moieties such as reduced Amadori products of other sugar-hemoglobin adducts, or mannitollysine residues. For convenience of expression, all of the reduced, stable hemoglobin (Amadori) products are referred to as glucitollysine residues, and thus receptor molecules that immunoreact with those reduced products are referred to as "glucitollysine-specific". The useful receptor molecules can also cross-react with other moieties such as sorbitol, mannitol, reduced Amadori products of plasma and other proteins, as well as free amino acids such as lysine or argine. However, those other moieties are absent from the immunoreaction admixture useful herein, so any additional cross-reactivities of the useful receptor molecules are not relevant to the present invention.

Methods for producing useful receptors that immunoreact with glucitollysine-hemoglobin and demonstrate little or no immunologic cross-reactivity with hemoglobin that does not contain glucitollysine residues; i.e., glucitollysine-specific receptor molecules, are well known in the art. Typically, those methods initially require producing an immunogen containing glucitollysine residues.

As previously discussed, methods for glycosylating proteins and synthetic polypeptides in general, and glucosylating those moieties in particular, are well known in the art. In addition, methods for converting lysine residues having glucose covalently bound to their epsilon amino groups into glucitollysine residues, as by reduction with a water-compatible borohydride reductant, are also well known in the art. See Curtiss et al., *J. Clin. Invest*, 72:1427–38 (1983). Furthermore, methods for producing receptors using protein and polypeptide immunogens are also well known in the art.

For example, Curtiss et al., supra, describe a method for making hybridomas that produce glucitollysine-specific monoclonal antibodies (receptors) using immunogens containing glucitollysine residues. Two hybridomas made by that method that secrete monoclonal antibodies that immunoreact with glucitollysine-hemoglobin but not glucohemoglobin or hemoglobin were deposited with the American Type Culture Collection (ATCC), Rockville, MD, pursuant to the Budapest Treaty on Sep. 20, 1983 under the following ATCC accession numbers:

| Hybridoma | Subclone | ATCC Accession No. |
|---|---|---|
| G6C9 | IC87G11 | HB 8356 |
| G8H9 | 2A1.5G8 | HB 8358 |

Monospecific antisera that immunoreact with glucitollysine-hemoglobin but demonstrate little cross-reactivity with hemoglobin that does not contain glucitollysine can also be prepared using well known immunoabsorption techniques. For example, glucitollysine-hemoglobin can be substituted for $HbA_{1c}$ as immunogen in the method described in U.S. Pat. No. 4,247,533 to Cerami et al., whose disclosure is incorporated herein by reference. Antibodies immunospecific for glucitollysine-hemoglobin can then be isolated; i.e., a monospecific antiserum can be produced, by using nonreduced hemoglobin and/or glucohemoglobin as an immunoabsorbent to absorb out cross-reactive antibodies. The testing procedures to monitor the production process use glucitollysine-hemoglobin as target antigen.

(g) The immunoreaction admixture is maintained under biological assay conditions for a predetermined time period, such as about 10 minutes to about 16–20 hours, preferably about 15 minutes to about 30 minutes, that is sufficient for the receptors to immunologically bind to the glucitollysine-hemoglobin present and form an immunoreactant.

Biological assay conditions are those that maintain the activity of the receptors and glucitollysine-hemoglobin sought to be assayed. Those conditions include a temperature range of about 4 degrees C. to about 45 degrees C., a pH value range of about 5 to about 9 and an ionic strength varying from that of distilled water to that of about one molar sodium chloride. Methods for optimizing such conditions are well known in the art.

(h) The amount of immunoreactant that formed in the immunoreaction admixture is then determined, and thereby the amount of stable glucohemoglobin present in the sample.

Determining the amount of immunoreactant formed, either directly or indirectly, can be accomplished by assay techniques well known in the art. For example, a homogeneous assay system can be used such as those described in U.S. Pat. No. 4,536,479; No. 4,233,401; No. 4,233,402 and No. 3,996,345, whose disclosures are incorporated herein by reference.

In preferred embodiments, the receptors of step (g), above, contain an indicating group or label capable of signaling the presence of the labeled receptor in an immunoreactant. Methods for assaying for the presence and amount of labeled receptors depend on the label used, such labels and assay methods being well known in the art.

The labeling of proteinaceous specific binding agents such as receptors is well known in the art. For instance, receptors produced by hybridomas can be labeled by metabolic incorporation of radioisotope-containing amino acids provided as a component in the tissue culture medium. See for example Galfre et al., *Meth. Enzymol.* 73, 3–46 (1981). The techniques of protein conjugation or coupling through activated functional groups are particularly applicable. See, for example, Aurameas, et al., *Scand. J. Immunol. Vol.* 8, Suppl. 7, 7-23 (1978) and U.S. Pat. No. 4,493,795, whose disclosures are incorporated herein by reference. In addition, a site-directed coupling reaction can be carried out so that the label does not substantially interfere with the immunoreaction of the second receptor with its target antigen. See, for example, Rodwell et al., *Biotech.* 3, 889-894 (1985).

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-lnaphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca,, "Immunofluorescence Analysis", in *Antibody As A Tool,* Marchalonis, et al., eds., John Wiley & Sons, Ltd., pp. 189-231 (1982), which is incorporated herein by reference.

In preferred embodiments, the indicating group is an enzyme, such as horseradish peroxidase (HRPO), glucose oxidase, or the like. In such cases where the principal indicating group is an enzyme such as HRPO or glucose oxidase, additional reagents are required to visualize the fact that a receptor-antigen complex (immunoreactant) has formed. Such additional reagents for HRPO include hydrogen peroxide ($H_2O_2$) and an oxidation dye precursor such as diaminobenzidine or o-phenylenediamine (OPD). An additional reagent useful with glucose oxidase is 2,2'-azino-di-(3-ethyl-benz-thiazoline-G-sulfonic acid) (ABTS).

Radioactive elements are also useful labeling agents and are used illustratively herein. An exemplary radiolabeling agent is a radioactive element that produces gamma ray emissions. Elements that themselves emit gamma rays, such as $^{124}I$, $^{125}I$, $^{128}I$, $^{131}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ that themselves emit positrons. The positrons so emitted produce gamma rays upon encounters with electrons present in the assay mixture. Also useful is a beta emitter, such as $^{111}In$ or $^3H$.

The indicating means can be linked directly to a receptor molecule useful in this invention or can comprise a separate molecule. The indicating means can be a separate molecule such as antibodies that bind to useful receptor molecules such as goat or rabbit anti-mouse antibodies. *Staphylococcus aureus* protein A, also can be used as a separate molecule indicator or labelling means where whole or substantially whole receptor molecules of this invention are utilized; i.e., where molecules containing the portion of the Fc regions of receptor molecules that are bound by protein A are used. In such uses, the protein A itself contains a label such as a radioactive element or a fluorochrome dye.

In particularly preferred practice, the before-described assay is carried out as a heterogeneous, solid phase assay in which the glucitollysine-containing antigen is bound or affixed to a solid phase matrix to form a solid phase support. The antigen can be bound or affixed to the solid matrix by any of a number of well known chemical or physical means. Although binding as by adsorption or immunoreaction is but one means of affixation, the words "bind" and "affix" and their various grammatical variants are utilized interchangeably herein.

Physical binding by adsorption of the antigen to the walls of microtiter plate wells utilized as solid phase matrices is illustrated hereinafter. Chemical binding means include binding by a first antibody that binds to a hemoglobin epitope that, when bound, does not substantially interfere with immunological binding of glucitollysine epitopes by the receptor molecules. This assay technique is usually referred to as a "sandwich" assay. Another chemical binding means utilizes a water-soluble carbodiimide reagent such as 1-ethyl-3-(3-dimethylaminopropyl)carbodiimide hydrochloride to form an amide or ester between a carboxylic acid of the matrix and an amino or hydroxyl group, respectively, of the receptor, or vice versa. Still further chemical binding means utilize polyfunctional reagents such as glutaraldehyde or cyanuric chloride, as are also well known.

Exemplary solid matrices useful in the above methods are well known in the art and include a solid matrix such as a 96-well microtiter plate sold under the designation Falcon Microtest III Flexible Assay Plates (Falcon Plastics, Oxnard, CA) or a microtiter strip containing twelve wells in a row, such as those strips sold under the designation Immulon I and II (Dynatech, Alexandria, VA). The microtiter strip or plate is made of a clear plastic material, preferably polyvinylchloride or polystyrene. Alternative solid matrices for use in a before-described method of this invention include polystyrene beads, about 1 micron to about 5 millimeters in diameter, available from Abbott Laboratories, North Chicago, IL; polystyrene tubes, sticks or paddles of any convenient size; and polystyrene latex whose polystyrene particles are of a size about 1 micron and can be centrifugally separated from the remainder of the latex.

The solid matrix also can be made of a variety of materials such as cross-linked dextran, e.g. Sephadex G-25, -50, -100, -200 and the like available from Pharmacia Fine Chemicals of Piscataway, NJ, agarose and cross-linked agarose, e.g. Sepharose 6B, CL6B, 4B, CL46 and the like also available from Pharmacia Fine Chemicals.

The before-described assay method can be used to determine the amount of any particular glycitollysine-hemoglobin species present in a hemoglobin sample as desired by using receptors immunospecific for the desired glycitollysine species.

D. Diagnostic Systems

Another aspect of the present invention is a diagnostic system that is typically in kit form, and is useful for carrying a before-described assay method. The system contains a plurality of packages.

A first package contains a solid phase matrix as before-described. That matrix is preferably a plastic microtiter plate or strip containing a plurality of wells, e.g., 96 or 12, on whose well surfaces a before-described assay method is carried out.

A second package contains a predetermined amount of the water-compatible borohydride reductant. This reagent is typically supplied as a dry powder.

A third package contains a known amount of appropriate glycitollysine-specific receptor molecules, preferably glucitollysine-specific receptors, such as those secreted by the hybridomas having ATCC accession numbers HB 8356 and HB 8358. Those receptor molecules are typically present as an aqueous composition or as a freeze-dried powder. In preferred embodiments, the receptors are supplied linked to an indicating group or label as discussed previously.

A fourth package contains a predetermined amount of phthalic acid or biphthalic acid. The acid can also be supplied dissolved in an aqueous medium or as a dry solid.

Preferred embodiments also include an additional package that contains a glycitollysine-hemoglobin species that immunoreacts with the receptors provided. Or preferably, the package contains glucitollysine-hemoglobin having a known percentage of glucitollysine to be used as a standard or control. Further packages that can also be included in the system include those containing buffer salts or solutions such as PBS, a separately packaged indicating means such as labeled protein A or labeled anti-receptor antibodies, separately packaged visualizing reagents for an enzyme indicating means such as hydrogen peroxide and an oxidative dye precursor, additional controls and the like.

It is to be understood that each package included in the system contains an amount of its contents that is sufficient to perform one assay, including appropriate controls. Preferably, an amount sufficient to carry out a plurality of assays is contained in each package.

BEST MODE FOR CARRYING OUT THE INVENTION

The following examples are intended to illustrate, but not limit, the present invention.

EXAMPLE 1

Hemoglobin Samples

Hemoglobin samples were obtained from 118 diabetes patients, both male and female, ranging in age between 18 and 88 years. Samples were also obtained from 35 normal adults (normoglucemic), both male and female, between 24 and 52 years of age. The samples were obtained from the Endocrinology and Diabetes Clinics of Scripps Clinic and Research Foundation, La Jolla., Calif. and from Kaiser Permanente, San Diego, Calif.

Blood samples were collected in tubes containing ethylenediaminetetraacetic acid (EDTA) as an anticoagulant, and were subjected to centrifugation at about 12,000–13,000×g for 3 minutes in a Beckman microfuge 12 to form a packed red blood cell (RBC) pellet and a plasma fraction. The plasma fraction was discarded and the hemoglobin sample to be assayed was typically provided as either 10 or 15 microliters of the pellet (packed RBCs).

To determine the number of milligrams of hemoglobin per microliter of a packed RBC pellet as obtained above, one volume of a pellet was admixed with either 1 volume or 3 volumes of Isoton III (Coulter Electronic, Inc., Hialeah, FL) to form 1:2 and 1:4 pellet dilutions, respectively. Each pellet dilution was then analyzed for hemoglobin concentration using a model S-Plus VI Coulter Counter (Coulter Electronics) according to the manufacturer's instructions. Briefly, the hemoglobin present in the dilutions was converted to cyanmethemoglobin using Drabkin's reagent, and the amount present was determined spectrophotometrically by the absorbance at 540 nanometers (nm).

The average number of milligrams (mg) of hemoglobin (Hb) per microliter (ul) of packed RBC pellet was found to be 0.294 mg Hb/ul. However, for ease in performing calculations, that value was rounded to 0.3 mg Hb/ul for all ratio determinations based on hemoglobin samples provided as a known volume of a packed red blood cell pellet.

When hemoglobin samples were provided as a known volume of whole blood, the amount of hemoglobin present was determined using an average value of 155 mg Hb/ml whole blood for samples obtained from males and 135 mg Hb/ml for female blood samples.

EXAMPLE 2

Production, Purification and Labeling of Receptors

The hybridoma having ATCC accession number HB 8356 produces the monoclonal antibody G6C9 as described in Curtiss et al., *J. Clin. Invest.* 72: 1427–38 (1983). Ascites tumor fluids containing G6C9 receptor molecules were obtained from 10-week old Balb/c mice, which had each been primed with 0.3 ml of mineral oil and injected intraperitoneally with $3-50\times10^5$ HB 8356 cells. The average time for development of ascites was 12 days. Following clarification by centrifugation at 15,000xg for 1 hour at 4 degrees C., ascites tumor fluids were pooled and stored frozen at −20 degrees C.

G6C9 Receptors were purified by subjecting the ascites tumor fluids to fast protein liquid chromatography (FPLC) on a Pharmacia Mono Q HR 5/5 anion exchange column in a Pharmacia FPLC. System using a 0–0.5 NaCl gradient in 10 mM Tris, pH 8.0, and following the directions supplied with the column.

The purified G6C9 receptor molecules were coupled to horseradish peroxidase using the method described in Nakane et al., *J. Histochem. Cytochem.*, 22:1084–1089 (1974). Those receptors are referred to hereinafter as HRPO-G6C9.receptors.

EXAMPLE 3

Preparation of Glucosylated Adducts

The following proteins and precursors were subjected to glucosylation and/or reduction: poly-L-lysine, poly-L-valine (Sigma Chemical Co., St. Louis, MO); Alpha-T-Boc-Lysine (Bachem, Torrance, CA); purified human hemoglobin, (Sigma); and glucitollysine prepared by the procedure described by Schwartz et al., *Arch. Biochem. Biophys.*, 181:542–549 (1977).

Glucosylated and reduced adducts are referred to as glc-RED adducts. The glc-RED adducts were prepared by admixing 2 milliliters (ml) of a 15 milligram per milliliter (mg/ml) solution of the various above-described proteins and precursors with 2 ml of 240 mM glucose (Sigma) in phosphate-buffered saline (PBS) and 2 ml of 37.5 mg/ml NaCNBH$_3$ (J. T. Baker Chemical Co, Phillipsburg, NJ) in PBS, pH 7.4. The resulting admixtures were maintained in sealed glass tubes (16×100 mm) for 120 hours at 37 degrees C. The adducts were subsequently transferred to dialysis bags (Spectraphor, molecular exclusion 3,500 mw) and exhaustively dialyzed against PBS for 72 hours at 4 degrees , adjusted to a final concentration of about 5 mg/ml and stored at 4 degrees C.

Glucosylated but non-reduced adduct controls (glc-NR) were prepared by substituting 2 ml PBS for the NaCNBH$_3$ in the above procedure. Non-glucosylated reduced controls (RED-adducts) were prepared by substituting 2 ml PBS for the 240 mM glucose in above procedure.

EXAMPLE 4

Determination of Antibody Specificity by Competitive Inhibition

The glc-RED, glc-NR and RED-adducts prepared in Example 3 were diluted to concentrations varying from 200 micrograms per milliliter (ug/ml) to 0.39 ug/ml in PBS containing 10% normal goat serum (NGS). Five hundred microliters (ul) of the various dilutions were then admixed in glass tubes with 500 ul of the HRPO-G6C9 receptors prepared in Example 2 (diluted 1:150 in PBS containing 10 percent NGS) to form competitive immunoreaction admixtures. The admixtures were maintained for one hour at 37 degrees C. to permit the receptors to immunmoplogically bind any glucitollysine residue-containing or non-glucitollysine containing but cross-reactive epitopes, and form a liquid phase immunoreactant.

The maintained competitive immunoreaction admixtures were subsequently assayed for the amount of nonbound HRPO-G6C9 receptors. This was accomplished using solid phase-affixed glucitollysine-hemoglobin as a target or capturing antigen in an ELISA.

Solid phase-affixed glucitollysine-hemoglobin was prepared by first admixing 0.240 ml of a packed RBC pellet prepared according to the procedure of Example 1 using the blood of a diabetic patient with 15 ml of distilled water containing 0.05 mM phthalic acid (a 1:62.5 dilution by volume). The resulting acid reaction admixture was maintained for 15 minutes at 37 degrees C. to form a hemolysate.

Subsequently, 50 microliters of the hemolysate were admixed with 50 microliters of 400 mM $NaBH_4$, in the wells of a microtiter plate (solid matrix). The resulting reduction reaction admixture was maintained for 15 minutes at 37 degrees C. to permit formation of glucitollysine-hemoglobin, which by the end of this maintenance time became affixed to the solid phase matrix to form solid phase-affixed glucitollysine-hemoglobin (solid support) and a liquid phase containing nonreacted borohydride and the remainder of the reduction reaction mixture. The solid and liquid phases of the resulting admixture were separated. The solid supports formed by the adsorbed glucitollysine-hemoglobin affixed to the solid matrix well walls were then washed 4 times with 350 ul of PBS containing 0.05% Tween 20 [polyoxyethylene (20) sorbitan monolaurate] to form isolated solid phase-affixed glucitollysine-hemoglobin.

A volume of 100 ul of each of the maintained HRPO-G6C9/adduct competitive immunoreaction admixtures was then admixed with solid phase-affixed glucitollysine-hemoglobin. The second liquid/solid phase immunoreaction admixture thus formed was maintained for 15 minutes at 37 degrees C. to permit any antibody molecules that had not immunoreacted with an adduct-inhibitor or control to immunologically bind the solid phase glucitollysine-hemoglobin and form a solid phase-affixed immunoreactant.

The solid and liquid phases were again separated, and any solid phase-affixed immunoreactants that formed were further separated from the liquid phases by decantation and washing each of the wells 4 times with washing solution (PBS containing 0.05 percent Tween 20). The amount of solid phase-affixed immunoreactant that formed was then determined by admixing 100 ul of freshly prepared HRPO substrate solution [0.0125% $H_2O_2$ and 0.67 mg/ml o-phenylenediamine (OPD) in distilled water] in each well. Color was allowed to develop at room temperature (about 20 to about 25 degrees C.) for 5 minutes. The substrate conversion (color-producing) reaction was then stopped by admixing 50 ul of 4 N $H_2SO_4$ to each well. The optical density (O.D.) of the solutions was determined at a wavelength of 490 nm using a Dynatech MR600 (Dynatech, Alexandria, VA) microtiter plate reader.

Figure 1:
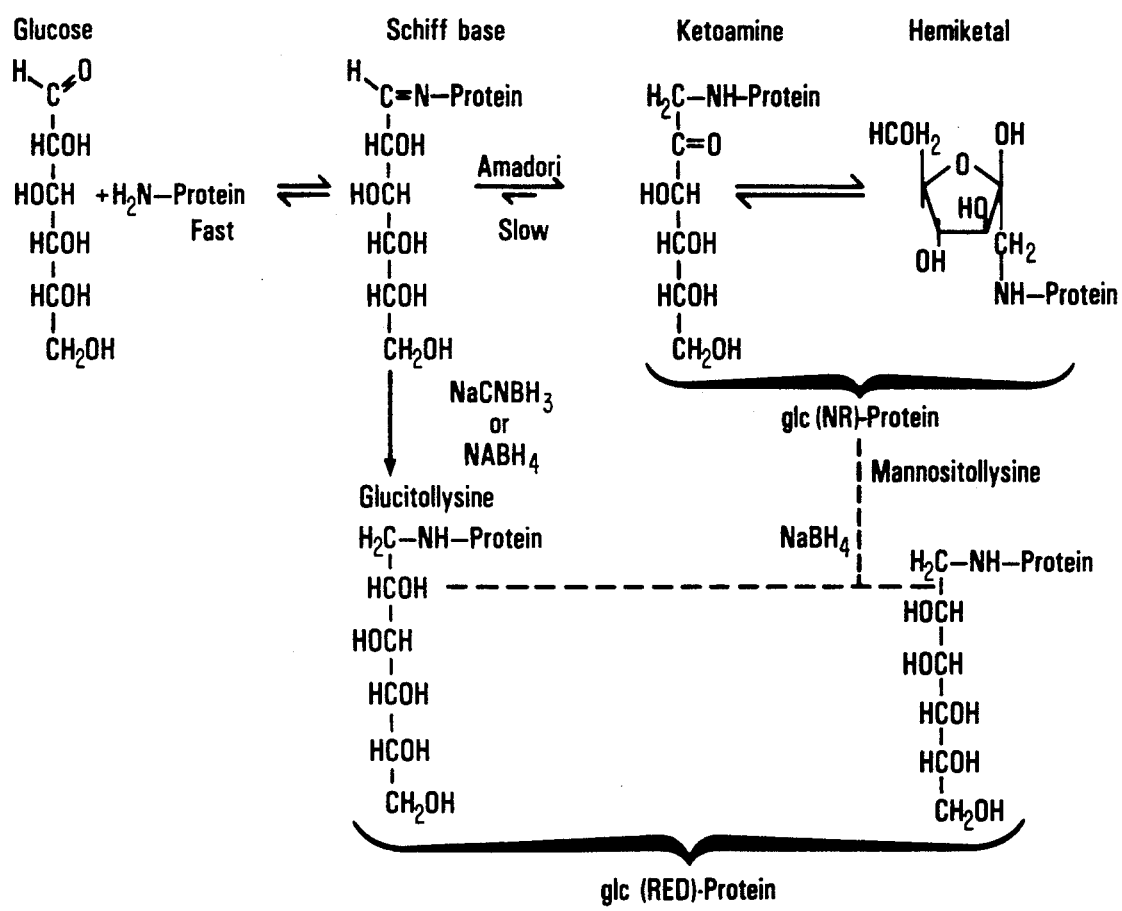
FIG. 1 is a schematic representation that illustrates the reaction sequence for the non-enzymatic glucosylation of the alpha (amino terminal valine) and epsilon (lysine) free amines of hemoglobin, designated as "protein" in the Figure, to form labile and stable glucohemoglobins, and the subsequent reduction of intermediates to form the glucitol-substituted final products.
Figure 2A:
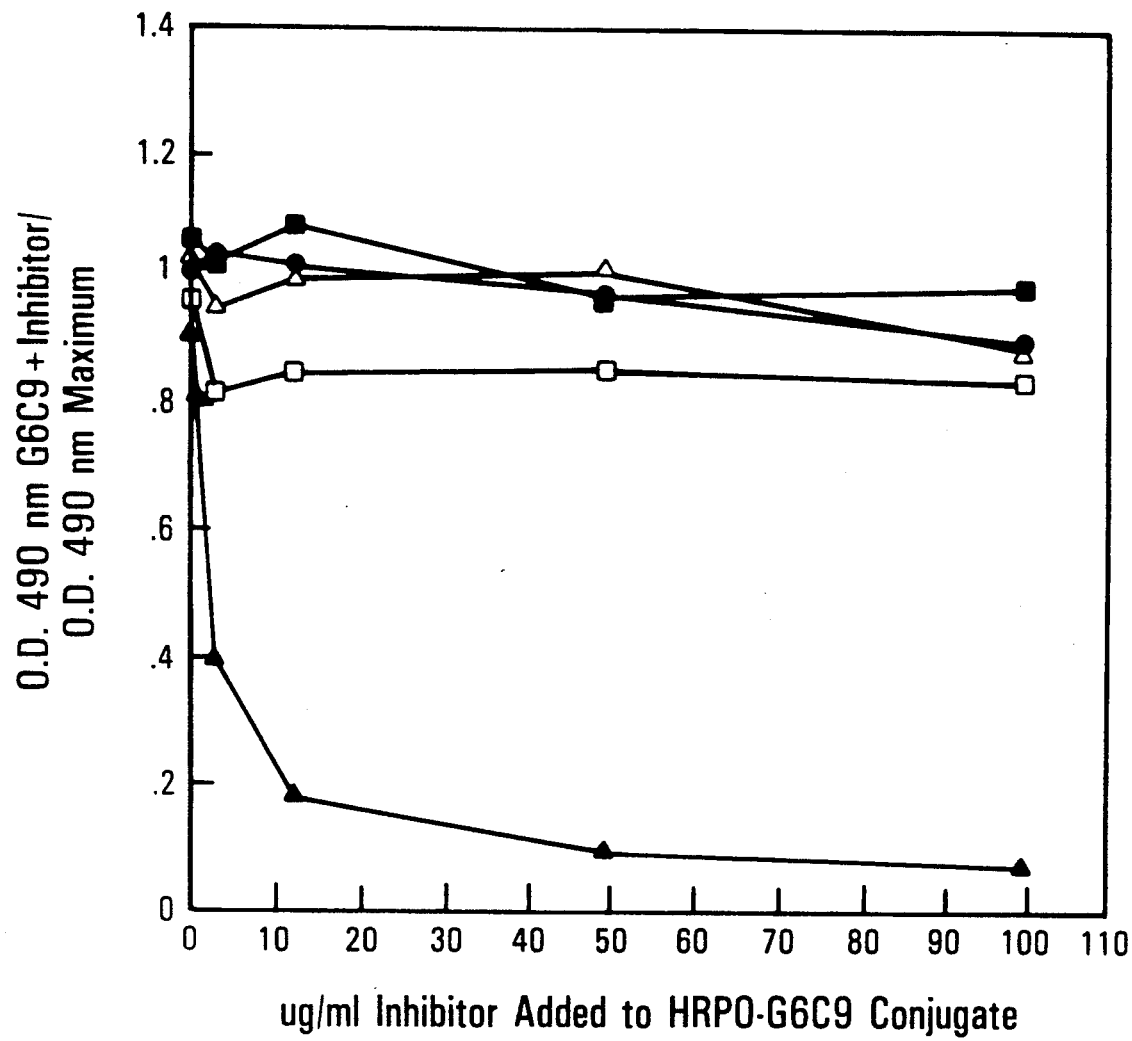
FIG. 2 contains three graph panels that illustrate the results of competitive inhibition studies performed by admixing horseradish peroxidase-labelled G6C9 receptors (HRPO-G6C9) with various concentrations of potential competitors for the G6C9 antibody combining site. The abscissa in each graph panel shows the concentration, in micrograms per milliliter (ug/ml), of the inhibitor solutions used. The ordinate in each graph panel shows the fraction of maximum binding; i.e., the amount of binding achieved by HRPO-G6C9 in the absence of competitive inhibitor, that remained or was achieved after reaction with the various potential inhibitors.
Figure 2B:
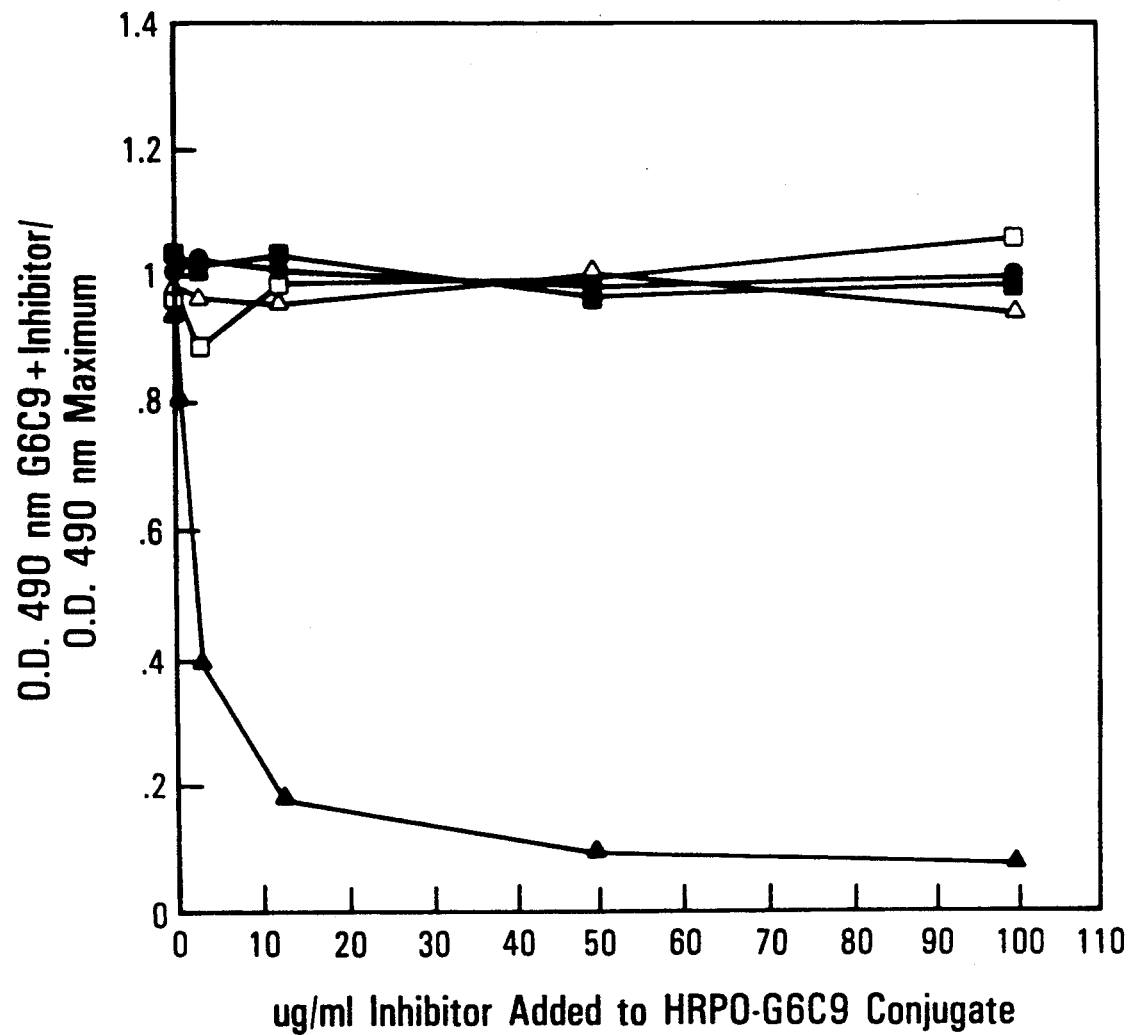
Figure 2C:
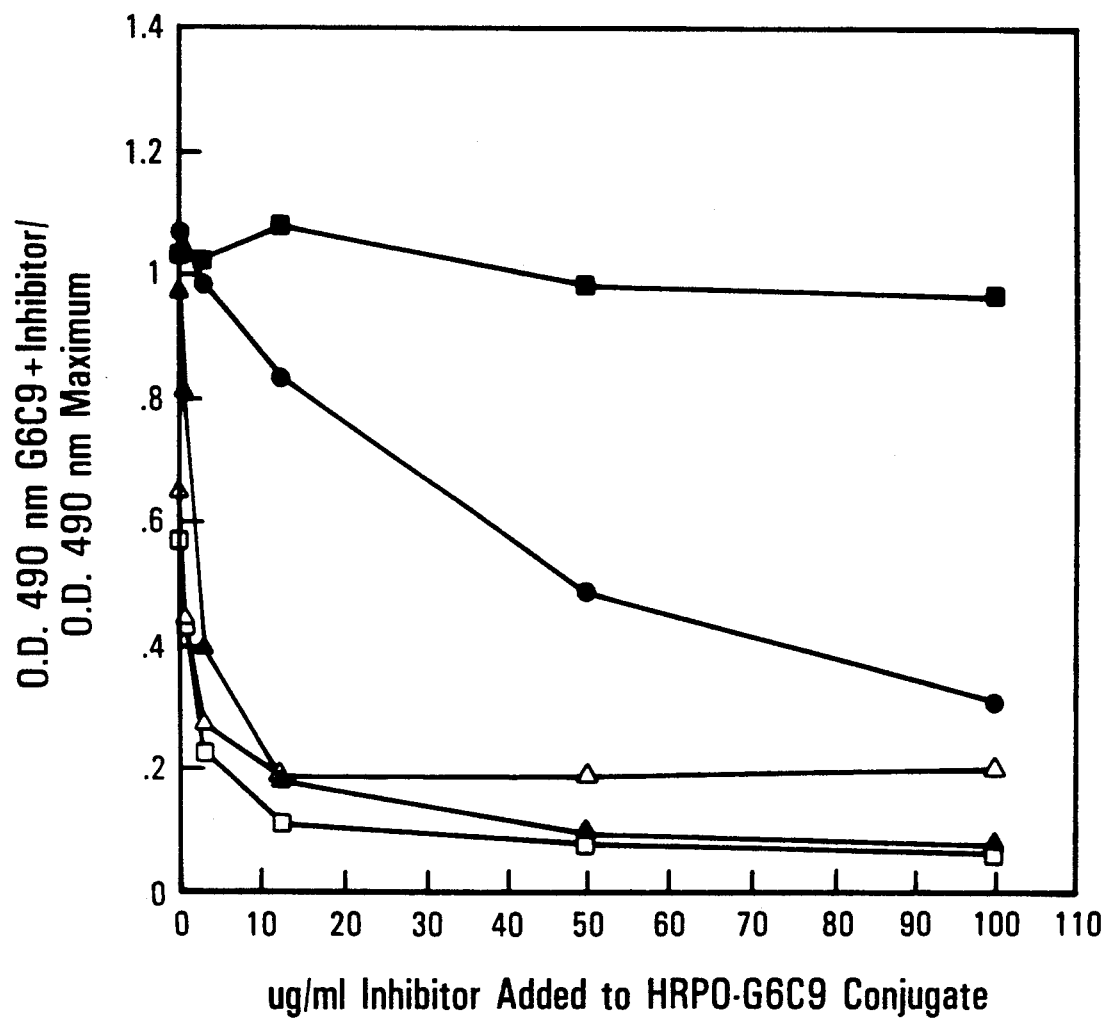

The results of this study are illustrated in FIGS. 2A, B and C. Those results indicate that the reduced but non-glucosylated adducts (FIG. 2A) and the glucosylated but non-reduced adducts (FIG. 2B) did not inhibit the binding of HRPO-G6C9 to the solid phase-affixed glucitollysine-hemoglobin. However, as illustrated in FIG. 2C, the glucosylated and reduced proteins and precursors containing lysine; i.e., glucitollysine, were very efficient inhibitors of the immunoreaction between HRPO-G6C9 and solid phase-affixed glucitollysine-hemoglobin, but glucosylated and reduced poly-L-Valine was not. Because the structural feature common to those adducts that inhibited the formation of solid phase immunoreactants was the presence of a glucitollysine residue, the results of this study demonstrate that G6C9 receptors immunoreact with a glucitollysine-containing epitope when that epitope is presented as solid phase-affixed glucitollysine-hemoglobin.

EXAMPLE 5

Reduction Optimization a. Water-Compatible Reductants

As previously described, glucitollysine is the reduced hexose alcohol form of glucose covalently bound to the epsilon amino group of lysine. The following studies were performed to examine different water-compatible borohydride reductants for their abilities to produce glucitollysine residues on hemoglobin under various conditions Hemoglobin samples were provided as 10 ul of a packed RBC pellet prepared as described in Example 1 (about 3 mg of hemoglobin) using blood from a normal individual and a diabetic individual. The percent of glycosylated hemoglobin in each sample was determined using the commercially available GLY-AFFIN GHb assay system (Isolab, Akron, OH) and were found to be 6.3 percent in the normal sample and 8.9 percent in the diabetic sample. Thus, there was about 1.4 times as much glucosylated hemoglobin in the diabetic sample as compared to the normal sample. The samples were each admixed with 615 ul of either distilled water or 0.05 M phthalic acid. This produced admixtures containing hemoglobin at a concentration of about 4.8 mg/ml and, where acid was used, a ratio of at least about 10 micromoles of acid per milligram of hemoglobin.

The resulting admixtures were maintained for 15 minutes at 37 degrees C. During that time period substantially all of the RBCs present in each admixture were lysed, thereby releasing the hemoglobin contained therein into solution and forming a hemolysate.

Subsequently, 50 ul of each hemolysate (about 0.24 mg of hemoglobin) were admixed in a microtiter plate well with 50 microliters of various concentrations of $NaBH_4$ or $KBH_4$ to form reduction reaction admixtures. Those admixtures were maintained for 15 minutes at 37 degrees C. During that time period the hemoglobin lysine residues having glucose covalently bound to their epsilon amino groups were reduced to form glucitollysine residues. In addition, the glucitollysine-hemoglobin that was formed was affixed by adsorption to the walls of the microtiter plate well; i.e., solid phase bound glucitollysine-hemoglobin was formed.

The solid and liquid phases were separated by decanting. Each of the wells was then washed 4 times with washing solution to further separate the nonreacted borohydride from the solid phase-affixed (microtiter plate well-bound) glucitollysine-hemoglobin.

To each well were then admixed 100 microliters of horseradish peroxidase-labeled G6C9 (HRPO-G6C9) receptors obtained in Example 2 to form an immunoreaction admixture. That admixture was maintained for 15 minutes at 37 degrees C., thereby permitting the labeled receptors to immunologically bind to the solid phase-affixed (microtiter plate well-bound) glucitollysine-hemoglobin present, and form a solid phase-affixed (microtiter plate well-bound) immunoreactant. Nonimmunoreacted (non-bound) HRPO-G6C9 was removed from the wells by decanting, followed by washing 5 times with washing solution. The amount of solid phase-bound immunoreactant that formed was then determined as described in Example 4.

Figure 3A:
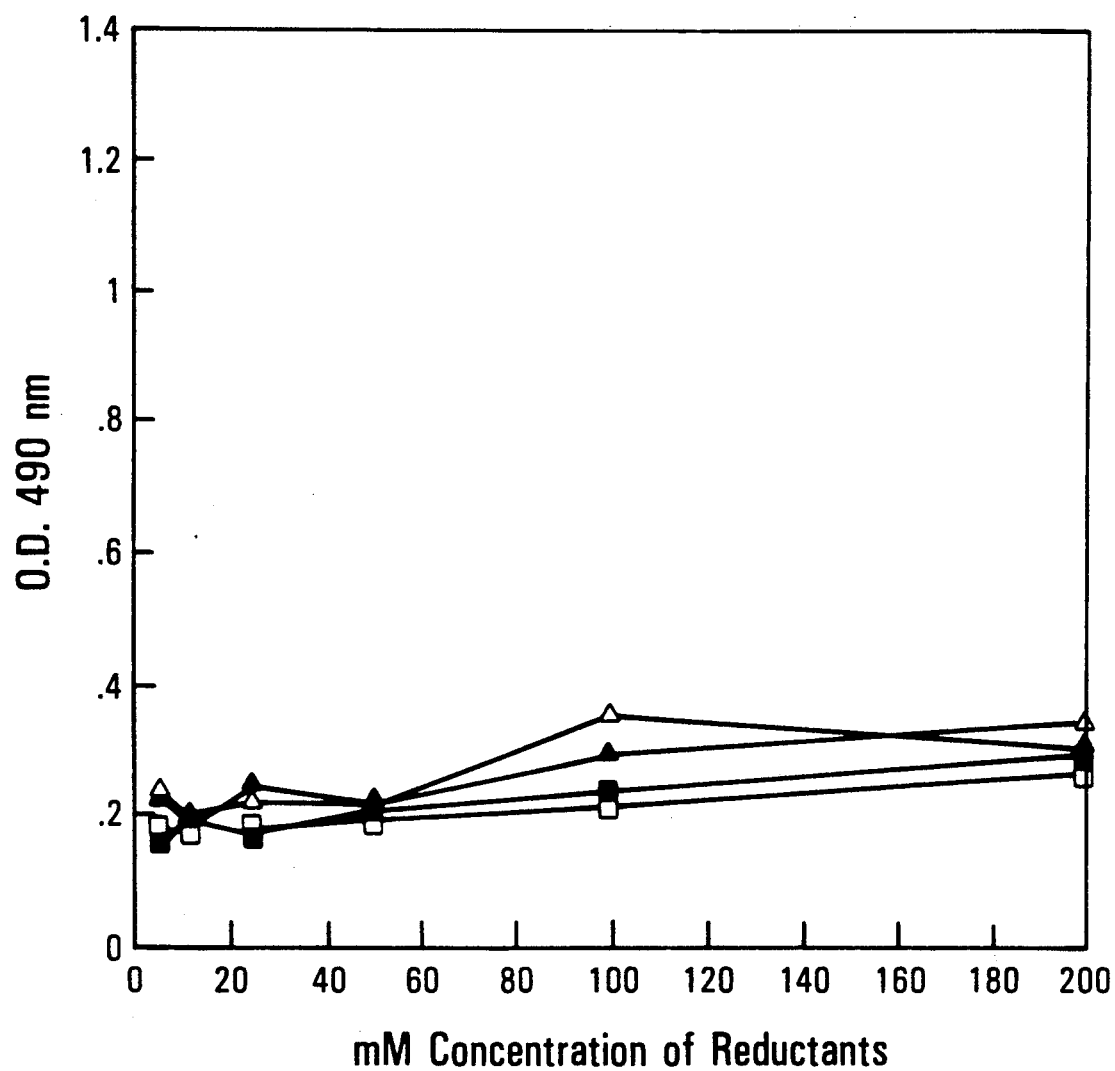

The results of this study are illustrated in FIGS. 3A and B, and demonstrate several phenomena of interest. First, as can be seen in both FIGS. 3A and 3B, there was no substantial difference between the results obtained using either sodium or potassium borohydrides as the water-compatible borohydride reductant.

Second, FIG. 3A demonstrates that reduction, (glucitollysine formation) in the absence of acid produces, as expected, a greater number of receptor-bound glucitollysine residue-containing epitopes in the sample containing the greater amount of glucohemoglobin; i.e., the diabetic sample. However, when those results are compared to the results obtained when reductions were performed in the presence of acid (FIG. 3B), it is seen that a greater number of receptor-bound glucitollysine residues were produced in both hemoglobin samples relative to the number produced in the absence of phthalic acid. In addition, there was a greater difference in the number of receptor-bound glucitollysine residues between the normal and diabetic samples when reduction was performed in the presence of phthalic acid (FIG. 3B) as compared to when it was performed in the absence of that acid (FIG. 3A). These two findings indicate that the presence of phthalic acid unexpectedly potentiates the ability of a water-compatible borohydride reductant to produce glucitollysine residue-containing epitopes as well as lyse the red blood cells and remove labile glucohemoglobin.

Figure 3B:
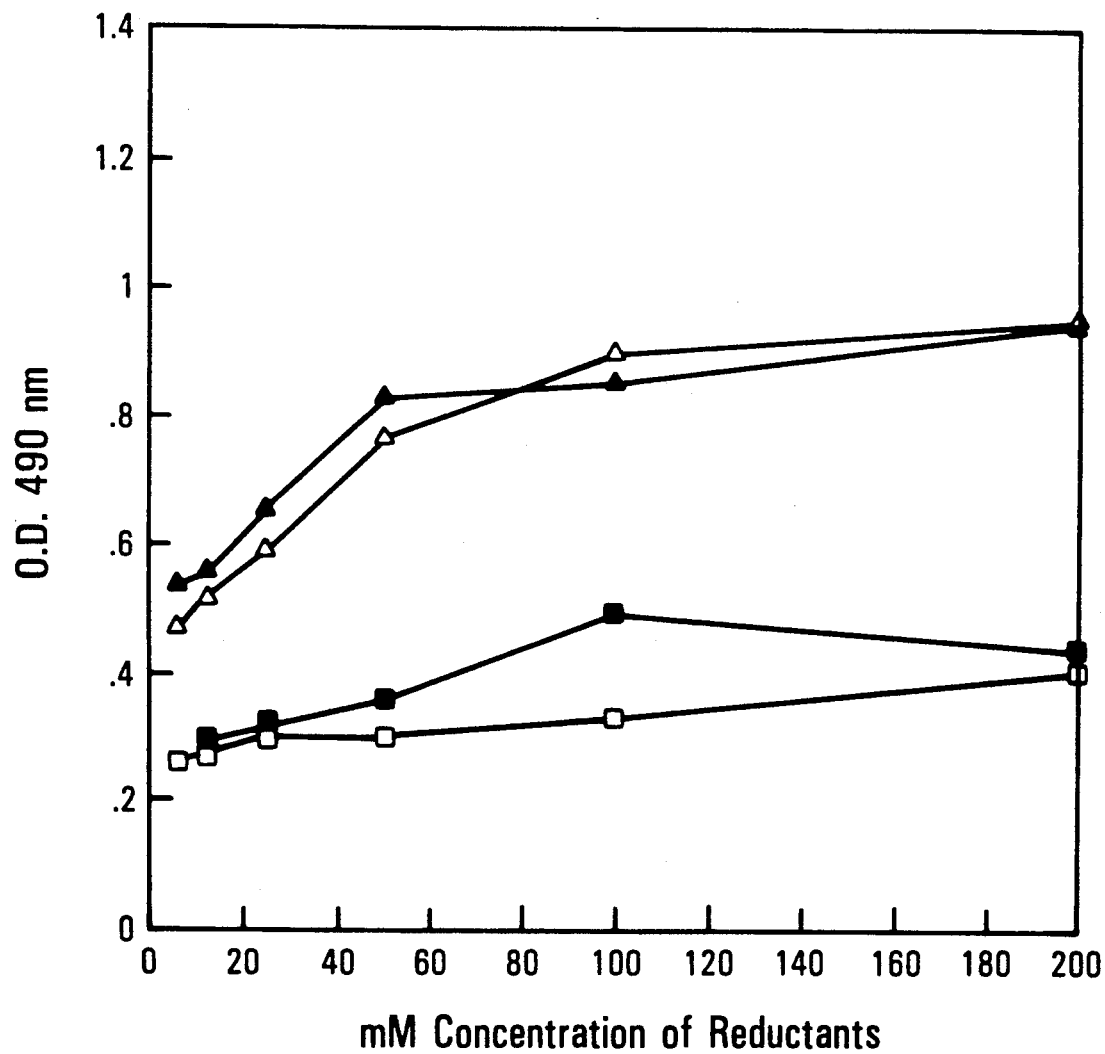

Finally, when the results in FIG. 3A are compared to those shown in FIG. 3B, it is seen that when the hemoglobin sample was admixed with phthalic acid at a ratio of at least about 10 micromoles of acid per milligram of hemoglobin, the reduction reaction was potentiated even when the hemoglobin was admixed with borohydride at a ratio as low as at least about 2.6 micromoles of borohydride per milligram hemoglobin.

The above-discussed findings were contrary to the teachings of the art and therefore unexpected. As discussed before, the art teaches that the total amount of glucohemoglobin in a hemoglobin sample obtained from RBCs is the sum of the labile and stable glucohemoglobin fractions. According to Bisse et al., Diabetes 31: 630–633 (1982), the labile fraction is depleted from a hemoglobin sample by treatment with biphthalic acid; i.e., the amount of assayable glucohemoglobin is decreased in a biphthalic acid-treated sample. Therefore, the art teaches that, in an assay that measures the amount of glucohemoglobin in a sample, the signal produced by a sample having its labile fraction depleted should be less than that produced by a comparable non-depleted sample.

b. Reduction Reaction Admixture Maintenance Period

Acid reaction admixtures were prepared using hemoglobin provided as whole blood samples from each of one diabetic and one normal females. The phthalic acid concentration in each admixture was a constant 0.05 M. However, the hemoglobin concentration varied over a range of 27.0 mg/ml to 0.270 ug/ml, thereby producing micromoles acid/mg Hb ratios ranging from 1.85 to 185.2. The acid reaction admixtures were all maintained for 15 minutes at 37 degress C. to form hemolysates.

Subsequently, reduction reaction admixtures were prepared in duplicate by admixing 50 microliters of each hemolysate and 50 microliters of 400 mM NaBH$_4$, thereby producing millimoles borohydride/mg Hb ratios ranging from 0.0148 to 1.481. One set of the reduction reaction admixtures was maintained for 15 minutes and the other for 30 minutes, each at 37 degrees C. The samples were thereafter separated from the unreacted borohydride and remaining reduction reaction admixture compositions, washed, and assayed for glucitollysine-hemoglobin as described in Example 4.

As seen in FIG. 4, the results of this study indicate that a reduction reaction maintenance period of either 15 or 30 minutes produces measurable amounts of glucitollysine-hemoglobin in both diabetic and normal samples at all hemoglobin concentrations examined. It should also be noted that the optimal ratios for production of assayable glucitollysine were found to be 46.3 micromoles acid/mg Hb for the acid reaction admixtures and 0.37 millimoles borohydride/mg Hb for the reduction reaction admixtures when hemoglobin was present at concentrations of 1.08 mg/ml and 0.54 mg/ml in the respective reactions.

EXAMPLE 6

Labile Glucohemoglobin Depletion a. Acid Reaction Admixtures

The dissociation of labile glucohemoglobin into glucose and hemoglobin has been reported to be acid catalyzed in solutions having a pH value of about 5. Bisse et al., Diabetes, 31:630–633 (1982). To determine if the reported pH-dependent stability of labile glucohemoglobin was affected by the type of acid used, solutions containing either phthalic acid, citrate, acetic acid, phosphate, D(+) glucosamine, alpha-ketoglutaric acid, oxalacetic acid, oxalic di-potassium acid, succinic acid or pyruvic acid were prepared at a concentration of 0.05 M and at a pH value within the range of 4 to 5. Hemoglobin samples provided as ten microliters of a packed RBC pellet were prepared as described in Example 1 from blood obtained from a diabetic and a normal individual. A diabetic and a normal hemoglobin sample were each admixed with 615 microliters of each of the above acidic solutions to form acid reaction admixtures or with 615 microliters of distilled water as a control.

In addition, packed RBC pellets were prepared from RBCs from both the diabetic and normal individuals that had been incubated overnight (about 8 hours) in isotonic saline. Ten microliters from each of those pellets were admixed with 615 microliters of either 0.05 M phthalic acid or distilled water as a control.

The acid reaction admixtures and control solutions so formed were maintained at 37 degrees C. for 15 minutes to form hemolysates. Glucitollysine-hemoglobin was subsequently formed and assayed using 50 microliter aliquots of each of the hemolysates, $NaBH_4$ and HRPO-G6C9 receptors as described in Example 4.

The results of this study are illustrated in FIG. 5. Those results indicate that reacting glucohemoglobin with phthatic acid prior to reduction with borohydride significantly potentiates the formation of glucitollysine-residues as compared to the other acids examined.

b. Acid Concentration

To examine the effect of phthalic acid concentration, within the pH 4-5 range, on glucitollysine-hemoglobin production and assay performance, acid reaction admixtures having phthalic acid concentrations of either 0.05 M or 0.025 M were prepared having hemoglobin concentrations of 75, 50, 7.5, 30, 25, or 21.4 milligrams hemoglobin per milliliter. Thus, in the admixtures containing 0.05 M phthalic acid there was a ratio range of micromoles of phthalic acid per milligram of hemoglobin of from 0.66 to about 2.34. Similarly, in the 0.025 M phthalic acid admixtures, the range of ratios was from 0.33 to 1.17. Hemoglobin was provided as a predetermined volume of a packed RBC pellet prepared from the blood of a diabetic individual as described in Example 1.

The resulting acid reaction admixtures were maintained for 15 minutes at 37 degrees C. to form hemolysates. Glucitollysine-hemoglobin was subsequently formed and assayed using 50 microliters of each of the hemolysates, $NaBH_4$ and HRPO-G6C9 receptors as described in Example 4.

FIG. 6 illustrates the results of this study. Those results indicate that both the 0.05 M and 0.025 M phthalic acid reaction admixutres potentiated the formation of glucitollysine residue-containing epitopes bound by labeled receptors when the ratio of micromoles as per milligram hemoglobin was between about 1.00 and about 2.34.

In addition, the results shown in FIG. 6 demonstrate that reaction with phthalic acid alone does not produce assayable glucitollysine.

c. Acid pH Value

Stock solutions containing 0.05 M phthalic acid having pH values of 3.5, 4.5, 5.5 and 6.5 were prepared. Four acid reaction admixtures were then prepared using each stock solution. Hemoglobin samples provided as 10 microliters of packed RBC pellets obtained as in Example 1 using each of two diabetic and two normal blood samples were admixed with 615 microliters of each stock solution. The resulting acid reaction admixtures were maintained for 15 minutes at 37 degrees C. to form hemolysates. Glucitollysine-hemoglobin was subsequently formed and assayed using 50 microliters of each of the hemolysates, $NaBH_4$ and HRPO-G6C9 receptors as described in Example 4.

FIG. 7 illustrates the results of this study, and shows that the greatest number of immunologically bindable glucitollysine residues were produced in assays performed on hemolysates formed using phthalic acid having a pH value of about 3.5. However, the pH value producing the greatest difference in signal (optical density) between the normal and diabetic samples was 4.5. Furthermore, the use of phthalic acid solutions having pH values of 5.5 and 6.5 also produced measurable amounts of glucitollysine residues.

To examine variability in the pH value of 0.05 M aqueous phthalic acid, four 0.05 M solutions were prepared and their non-adjusted pH values determined using an Altex model 3500 digital pH meter (Beckman Instruments, Berkeley, CA), in combination with a Calomel MicroProbe electrode (Fisher Scientific, Pittsburgh, PA). The pH values found for the four non-adjusted solutions ranged from 4.13 to 4.5 and had an average of about 4.3.

d. Acid Reaction Admixture Maintenance Time

One purpose of the acid reaction step in the assay method of the present invention is to deplete the labile glucohemoglobin fraction (dissociate the labile glucohemoglobin into hemoglobin and glucose) while maintaining the stable fraction. The effect of varying the acid reaction admixture maintenance time period was therefore examined.

Four sets of acid reaction admixtures were studied. Each set contained four admixtures prepared by admixing a hemoglobin sample from each of the 2 diabetic and 2 normal female blood samples with 0.05 M phthalic acid as described in Example 6c. One of the acid reaction admixture sets was then immediately admixed with $NaBH_4$ and further processed and assayed as described in Example 4. The remaining 3 sets were maintained for a time period of 5, 10 or 15 minutes prior to being admixed with $NaBH_4$ as in Example 4.

The results of this study, as seen in FIG. 8, indicate that an increase in the acid reaction admixture maintenance time period resulted in the formation of less assayable glucitollyisine in diabetic sample number 1, thus indicating that that sample initially contained a substantial amount of labile glucohemoglobin. The 15-minute maintenance time also produced less assayable glucitollysine in diabetic sample number 2 and normal sample number 1 as compared to the less than one minute time period. These results indicate that an acid reaction admixture maintenance time period as short as about 5 minutes can result in depletion of the labile glucohemoglobin fraction in a hemoglobin sample.

EXAMPLE 7

Assay Temperature

Hemolysates having hemoglobin concentrations ranging from 27 ug/ml to 1.35 ug/ml were prepared according to Example 5b using whole blood from diabetic and normal females. The hemolysates were then reduced and assayed at either room temperature (about 20–25 degrees C.) or 37 degrees C. as described in Example 4 using 30 minute maintenance periods for the reduction and antibody reactions.

FIG. 9 illustrates that whereas the amount of glucitollysine-hemoglobin detected was slightly greater when the reduction and immunoreaction admixtures were maintained at 37 degrees C., there was no substantial difference between the 37 degrees results and those obtained at room temperature.

EXAMPLE 8

ELISA Evaluation

Although the method of optimizing the production of assayable of glucitollysine residues on glucohemoglobin using phthalic acid and borohydride as described herein is applicable to any immunoassay format, the performance characteristic of an ELISA using that method were evaluated in detail to determine clinical utility as described hereinbelow. The particular ELISA format evaluated was performed as follows:

Ten microliters of a packed RBC pellet prepared as described in Example 1 using blood from various normal and diabetic individuals were admixed with 615 ul of 0.05 M potassium biphthalate. The acid reaction admixture so formed was maintained for 15 minutes at 37 degrees C. to form a hemolysate. Subsequently, 50 microliters of the hemolysate were pipetted into each of 3 NUNC Immuno I microtiter plate wells (flat bottom polystyrene plates, (Gibco Laboratory, Lawrence, MA). A volume of 50 mcroliters of 400 mM $NaBH_4$ was then admixed to each hemolysate sample to form reduction reaction admixtures. The obtained reduction reaction admixtures were maintained 15 minutes at 37 degrees C. to produce glucitollysine-hemoglobin bound to the microtiter plate wells. The microtiter plate well-bound glucitollysine-hemoglobin was separated from the excess borohydride by decanting and washing the wells 4 times with 0.35 ml of PBS containing 0.05% Tween 20.

The amount of well-bound glucitollysine-hemoglobin was then determined by admixing in each well 0.100 ml of the HRPO-G6C9 receptors of Example 2 diluted 1:300 in PBS containing 10 percent normal goat serum to form a liquid/solid phase immunoreaction admixture. The immunoreaction admixture was maintained for 15 minutes at 37 degrees C. The solid and liquid phases were separated and wells were then washed 5 times with 0.35 ml of PBS (pH 7.4) containing 0.05 percent Tween 20 to separate nonbound receptors from the solid phase affixed immunoreactants. HRPO-G6C9 receptors present as solid phase-affixed immunoreactants were detected using the OPD substrate solution as described in Example 4.

The Glc-RED Hb adduct prepared in Example 3 was used as an internal standard (calibrator) for the ELISA. Standard solutions were prepared ranging in concentration from 380 ug/ml to 8 ug/ml of Glc-RED hemoglobin Hb diluted in 0.1 M sodium bicarbonate buffer, pH 9.0, containing 10 percent normal goat serum. To generate a standard curve, the above-described ELISA was performed using 50 microliters of each standard solution in place of the hemolysate.

a. Recovery

Recovery studies were performed to determine if the ELISA could accurately measure various quantities of glucohemoglobin from a diabetic erythrocyte hemolysate added to a hemolysate from a normal individual. This was accomplished by preparing a hemolysate from a normal individual that contained various increasing percent additions (spikes) of a hemolysate from a diabetic individual.

Recovery of the amount of diabetic glucohemoglobin added to the hemolysate of the normal individual was then determined using the above-described ELISA. As shown in FIG. 10 the obtained results demonstrate a linear relationship over the range of percent additions (spikes) assayed, thus indicating an additive relationship between the amount of glucohemoglobin present in a sample and the amount of glucitollysine-hemoglobin determined by the ELISA.

b. Reproducibility of ELISA Results

The reproducibility of the ELISA was determined by intra-assay and inter-assay studies. For intra-assay determinations, hemoglobin samples from three different individuals were assayed 60 times each. The coefficient of variation among the values obtained for each individual ranged from 1.6 percent to 6.4 percent.

For inter-assay determinations, hemoglobin samples from 3 different individuals were assayed on 12 different occasions. The inter-assay reproducibility was determined to range from 8.3 percent to 10.4 percent.

The present invention has been described with respect to preferred embodiments. It will be clear to those skilled in the art that modifications and/or variations of the disclosed subject matter can be made without departing from the scope of the invention set forth herein.

What is claimed is:

1. A method of converting stable glucohemoglobin to glucitollysine-hemoglobin from a glucohemoglobin sample containing both labile and stable glucohemoglobins comprising the steps of:
   (a) admixing said sample with phthalic acid in an aqueous medium having a pH value of about 3 to about 6, at a ratio of at least about 1.5 micromoles of said acid per milligram of hemoglobin to form an acid reaction admixture;
   (b) maintaining said acid reaction admixture for a predetermined time period at a temperature above 0 degrees C. to about 37 degrees C. sufficient to remove the labile glucohemoglobin present, while maintaining the stable glucohemoglobin present in the original sample;
   (c) admixing said acid reaction admixture with a water-compatible borohydride reductant at a ratio of at least about 0.015 millimoles of borohydride per milligram of hemoglobin to form a reduction reaction admixture;
   (d) maintaining said reduction reaction admixture for a predetermined time period at a temperature above about 0 degrees C. to about 37 degrees C. sufficient to form glucitollysine-hemoglobin; and
   (e) separating said glucitollysine-hemoglobin from any unreacted borohydride to form isolated glucitollysine-hemoglobin.

2. The method of claim 1 wherein said admixing of step (a) is carried out at a ratio of at least about 15 micromoles of acid per milligram of hemoglobin.

3. The method of claim 1 wherein said acid solution of step (a) has a pH value of about 4 to about 5.

4. The method of claim 1 wherein said admixing of step (c) is carried out at a ratio of at least about 0.15 millimoles of borohydride per milligram of hemoglobin.

5. The method of claim 1 wherein said sample is in the form of red blood cells.

* * * * *

UNITED STATES PATENT AND TRADEMARK OFFICE
CERTIFICATE OF CORRECTION

PATENT NO.    : 5,169,937
DATED         : December 8, 1992
INVENTOR(S)   : Richard Smith, Peta-Maree Lamb, Linda K. Curtiss and Joseph Witztum It is certified that error appears in the above-identified patent and that said Letters Patent is hereby corrected as shown below:

<u>Column 1,</u>
Line 5, insert:

-- This invention was made with government support under Grant No. HL 14197 from the National Institutes of Health. The U.S. government may have certain rights in the invention. --

Signed and Sealed this

Twenty-first Day of May, 2002

Attest:

Attesting Officer

JAMES E. ROGAN
*Director of the United States Patent and Trademark Office*